(12) United States Patent
Allen et al.

(10) Patent No.: US 7,456,177 B2
(45) Date of Patent: Nov. 25, 2008

(54) HETEROARYL FUSED AZAPOLYCYCLIC COMPOUNDS

(75) Inventors: Martin P. Allen, North Stonington, CT (US); Jotham W. Coe, Niantic, CT (US); Spiros Liras, Stonington, CT (US); Christopher J. O'Donnell, Mystic, CT (US); Brian T. O'Neill, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 284 days.

(21) Appl. No.: 10/889,395

(22) Filed: Jul. 12, 2004

(65) Prior Publication Data

US 2005/0020830 A1    Jan. 27, 2005

Related U.S. Application Data

(60) Provisional application No. 60/488,760, filed on Jul. 21, 2003.

(51) Int. Cl.
*A61K 31/502* (2006.01)
*C07D 471/02* (2006.01)

(52) U.S. Cl. .................. 514/248; 544/233; 544/95; 546/63; 435/184; 514/229.5; 514/286

(58) Field of Classification Search .................. 514/248, 514/229.5, 286; 544/233, 95; 546/63; 435/184
See application file for complete search history.

(56) References Cited

U.S. PATENT DOCUMENTS 6,462,035 B1 * 10/2002 Coe ........................... 514/183

\* cited by examiner

*Primary Examiner*—Charanjit S. Aulakh
(74) *Attorney, Agent, or Firm*—Steve T. Zelson; Stuart P. Suskind

(57) ABSTRACT

The present invention provides a compound having the structure of formula I:

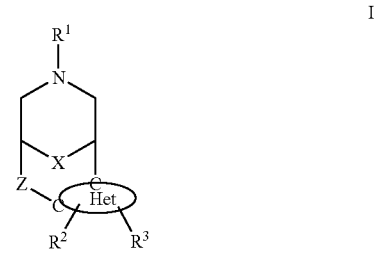

wherein $R^1$ is hydrogen, $(C_1–C_6)$ alkyl, unconjugated $(C_3–C_6)$ alkenyl, benzyl, $YC(=O)(C_1–C_6)$ alkyl or $—CH_2CH_2—O—(C_1–C_4)$ alkyl; X is $CH_2$ or $CH_2CH_2$; Y is $(C_2–C_6)$ alkylene; Z is $(CH_2)_m$, $CF_2$, or $C(=O)$, where m is 0, 1 or 2; $R^2$ and $R^3$ are selected independently from hydrogen, halogen, $—(C_1–C_6)$ alkyl optionally substituted with from 1 to 7 halogen atoms, and $—O(C_1–C_6)$ alkyl optionally substituted with from 1 to 7 halogen atoms, or $R^2$ and $R^3$ each together with the atom to which it is connected independently form $C(=O)$, $S\rightarrow O$, $S(=O)_2$, or $N\rightarrow O$; and Het is a 5- to 7-membered monocyclic heteroaryl group selected from pyridinyl, pyridone, pyridazinyl, imidazolyl, pyrimidinyl, pyrazolyl, triazolyl, pyrazinyl, furyl, thienyl, isoxazolyl, thiazolyl, oxazolyl, isothiazolyl, pyrrolyl, cinnolinyl, triazinyl, oxadiazolyl, thiadiazolyl and furazanyl groups.

3 Claims, No Drawings

HETEROARYL FUSED AZAPOLYCYCLIC COMPOUNDS

This application claims the benefit of provisional application Ser. No. 60/488,760, filed Jul. 21, 2003.

The subject invention relates to heteroaryl fused azapolycyclic compounds, pharmaceutical compositions comprising such compounds and methods of using such compounds to treat disease states, disorders and conditions mediated by neuronal nicotinic acetylcholine specific receptor sites. In particular, the subject invention relates to using such derivatives to reduce nicotine addiction or aiding in the cessation or lessening of tobacco use in a mammal.

The subject invention relates to certain heteroaryl fused azapolycyclic compounds defined in formulas I–VI below which bind to neuronal nicotinic acetylcholine specific receptor sites, and which are useful in modulating cholinergic function. These compounds are specifically useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD), attention deficit disorder (ADD), restless legs syndrome (RLS), mild cognitive impairment, cognitive enhancement in schizophrenia, drug induced extrapyramidal symptoms, conduct disorder, oppositional defined disorder, anxiety in anxious smokers, cardiovascular risk in pregnancy, delayed ejaculation, emesis, symptoms due to injury inflicted by biological warfare, diarrhea, nicotine gum addiction, sleep prevention, ischemia, and Tourette's Syndrome.

The compounds of this invention may also be used in combination with an antidepressant such as, for example, a tricyclic antidepressant or a serotonin reuptake inhibiting antidepressant (SRI), in order to treat both the cognitive decline and depression associated with AD, PD, stroke, Huntington's chorea or traumatic brain injury (TBI); in combination with muscarinic agonists in order to stimulate both central muscarinic and nicotinic receptors for the treatment, for example, of ALS, cognitive dysfunction, age-related cognitive decline, AD, PD, stroke, Huntington's chorea and TBI; in combination with neurotrophic factors such as NGF in order to maximize cholinergic enhancement for the treatment, for example, of ALS, cognitive dysfunction, age-related cognitive decline, AD, PD stroke, Huntington's chorea and TBI; or in combination with agents that slow or arrest AD such as cognition enhancers, amyloid aggregation inhibitors, secretase inhibitors, tau kinase inhibitors, neuronal anti-inflammatory agents and estrogen-like therapy.

Other compounds that bind to neuronal nicotinic receptor sites are referred to in WO 9818798 A1 (U.S. Pat. No. 6,235,734), WO 9935131-A1 (U.S. Pat. No. 6,410,550), U.S. Pat. No. 6,020,335 and WO9955680-A1 (U.S. Pat. No. 6,462,035). The foregoing applications are owned in common with the present application, and are incorporated herein by reference in their entirety.

SUMMARY OF THE INVENTION

The subject invention is directed to compounds of formula I:

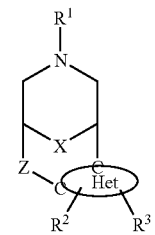

wherein $R^1$ is hydrogen, $(C_1–C_6)$ alkyl, unconjugated $(C_3–C_6)$ alkenyl, benzyl, $YC(=O)(C_1–C_6)$ alkyl or $—CH_2CH_2—O—(C_1–C_4)$ alkyl; wherein X is $CH_2$ or $CH_2CH_2$; wherein Y is $(C_2–C_6)$ alkylene;

wherein Z is $(CH_2)_m$, $CF_2$, or $C(=O)$, where m is 0, 1 or 2; wherein $R^2$ and $R^3$ are selected independently from hydrogen, halogen, $—(C_1–C_6)$ alkyl optionally substituted with from 1 to 7 halogen atoms, and $—O(C_1–C_6)$ alkyl optionally substituted with from 1 to 7 halogen atoms, or $R^2$ and $R^3$ each together with the atom to which it is connected independently form $C(=O)$, $S→O$, $S(=O)_2$, or $N→O$; and

is a 5- to 7-membered monocyclic heteroaryl group selected from pyridinyl, pyridone, pyridazinyl, imidazolyl, pyrimidinyl, pyrazolyl, triazolyl, pyrazinyl, furyl, thienyl, isoxazolyl, thiazolyl, oxazolyl, isothiazolyl, pyrrolyl, cinnolinyl, triazinyl, oxadiazolyl, thiadiazolyl and furazanyl groups; or

is a 8- to 11-membered fused bicyclic heteroaryl group selected from quinolyl, isoquinolyl, indolyl, benzimidazolyl, benzofuranyl, benzodiazapine, indazolyl, indolizinyl, phthalazinyl, isoindolyl, purinyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl groups.

The present invention also provides the compound having the structure of formula II:

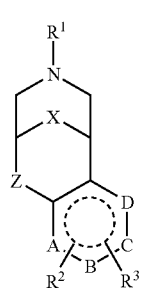

II wherein A, B, C and D are independently C, N, O or S, with the proviso that (a) at least one of A, B, C and D is N, O or S, (b) no adjacent pair thereof consists solely of O, and (c) A, B and C are not all S or N; or wherein only A, B, and C are present whereby a five-membered ring is provided thereby; wherein X is $(C_1-C_3)$alkylene; Y is $(C_1-C_6)$alkylene; wherein Z is $(CH_2)_m$, $CF_2$, or $C(=O)$, where m is 0, 1 or 2; wherein the dashed circle represents either an aromatic ring, one isolated double bond, two or three double bonds, either conjugated or unconjugated, or a fully saturated ring;

wherein $R^1$ is hydrogen, $(C_1-C_6)$ alkyl, unconjugated $(C_3-C_6)$alkenyl, benzyl, $Y'C(=O)(C_1-C_6)$ alkyl or —$CH_2CH_2$—O—$(C_1-C_4)$ alkyl, where Y' is $(C_1-C_4)$alkylene;

wherein $R^2$ and $R^3$ are selected, independently, from hydrogen, $(C_2-C_6)$alkenyl, $(C_2-C_6)$alkynyl, hydroxy, nitro, amino, halo, cyano, —$SO_q(C_1-C_6)$alkyl wherein q is zero, one or two, $(C_1-C_6)$alkylamino-, $[(C_1-C_6)alkyl]_2$amino-, —$CO_2R^4$, —$CONR^5R^6$, —$SO_2NR^7R^8$, —$C(=O)R^{13}$, —$XC(=O)R^{13}$, aryl-$(C_1-C_3)$alkyl- or aryl-$(C_1-C_3)$alkyl-O—, wherein said aryl is selected from phenyl and naphthyl, heteroaryl-$(C_1-C_3)$alkyl- or heteroaryl-$(C_1-C_3)$alkyl-O—, wherein said heteroaryl is selected from five to seven membered aromatic rings containing from one to four heteroatoms selected from oxygen, nitrogen and sulfur; $X^2(C_1-C_6)$alkyl- and $X^2(C_1-C_6)$alkoxy-$(C_1-C_6)$alkyl-, wherein $X^2$ is absent or $X^2$ is $(C_1-C_6)$alkylamino- or $[(C_1-C_6)alkyl]_2$amino-, and wherein the $(C_1-C_6)$alkyl- or $(C_1-C_6)$alkoxy-$(C_1-C_6)$alkyl-moieties of said $X^2(C_1-C_6)$alkyl- or $X^2(C_1-C_6)$alkoxy-$(C_1-C_6)$alkyl- contains at least one carbon atom, and wherein from one to three of the carbon atoms of said $(C_1-C_6)$alkyl- or $(C_1-C_6)$alkoxy-$(C_1-C_6)$alkyl- moieties may optionally be replaced by an oxygen, nitrogen or sulfur atom, with the proviso that any two such heteroatoms must be separated by at least two carbon atoms, and wherein any of the alkyl moieties of said $(C_1-C_6)$alkyl- or $(C_1-C_6)$alkoxy-$(C_1-C_6)$ alkyl- groups may be optionally substituted with from two to seven fluorine atoms, and wherein one of the carbon atoms of each of the alkyl moieties of said aryl-$(C_1-C_3)$alkyl- and said heteroaryl-$(C_1-C_3)$alkyl- may optionally be replaced by an oxygen, nitrogen or sulfur atom, and wherein each of the foregoing aryl and heteroaryl groups may optionally be substituted with one or more substituents, preferably from zero to two substituents, independently selected from $(C_1-C_6)$alkyl optionally substituted with from one to seven fluorine atoms, $(C_1-C_6)$alkoxy optionally substituted with from two to seven fluorine atoms, chloro, fluoro, bromo, iodo, $(C_2-C_6)$alkenyl, $(C_2-C_6)$alkynyl, hydroxy, nitro, cyano, amino, $(C_1-C_6)$alkylamino-, $[(C_1-C_6)alkyl]_2$amino-, —$CO_2R^4$, —$CONR^5R^6$, —$SO_2NR^7R^8$, —$C(=O)R^{13}$ and —$XC(=O)R^{13}$;

or wherein $R^2$ and $R^3$, together with the atoms to which they are attached, form a four to seven membered monocyclic, or ten to fourteen membered bicyclic, carbocyclic ring that can be saturated or unsaturated, wherein from one to three of the nonfused carbon atoms of said monocyclic rings, and from one to five of the carbon atoms of said bicyclic rings that are not part of the aromatic ring, may optionally and independently be replaced by a nitrogen, oxygen or sulfur, and wherein said monocyclic and bicyclic rings may optionally be substituted with one or more substituents that are selected, independently, from $(C_1-C_6)$ alkyl optionally substituted with from one to seven fluorine atoms; $(C_1-C_6)$ alkoxy optionally substituted with from one to seven fluorine atoms; nitro, cyano, halo, $(C_2-C_6)$alkenyl, $(C_2-C_6)$alkynyl, hydroxy, amino, $(C_1-C_6)$alkylamino and $((C_1-C_6)alkyl)_2$ amino, —$CO_2R^4$, —$CONR^5R^6$, —$SO_2NR^7R^8$, —$C(=O)R^{13}$ and —$X'C(=O)R^{13}$;

wherein each $R^4$, $R^5$, $R^6$, $R^7$, $R^8$ and $R^{13}$ is selected independently from hydrogen and $(C_1-C_6)$ alkyl, or $R^5$ and $R^6$, or $R^7$ and $R^8$ together with the nitrogen to which they are attached, form a pyrrolidine, piperidine, morpholine, azetidine, piperazine, —N—$(C_1-C_6)$alkylpiperazine or thiomorpholine ring, or a thiomorpholine ring wherein the ring sulfur is replaced with a sulfoxide or sulfone;

or a pharmaceutically acceptable salt thereof.

The present invention also provides the compound of formula II, wherein $R^2$ and $R^3$, together with the ABCD ring of formula II, form a bicyclic ring system selected from the following:

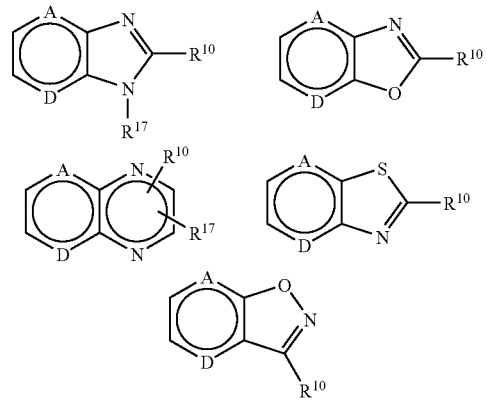

wherein $R^{10}$ and $R^{17}$ are selected independently from hydrogen, $(C_1-C_6)$alkyl, and $(C_1-C_6)$alkoxy-$(C_1-C_6)$alkyl-, wherein the total number of carbon atoms in the $(C_1-C_6)$ alkoxy-$(C_1-C_6)$alkyl- does not exceed six, and wherein any of the above alkyl moieties may optionally be substituted with from one to seven fluorine atoms; nitro, cyano, halo, amino, $(C_1-C_6)$alkylamino-, $[(C_1-C_6)$ alkyl]$_2$amino, —$CO_2R^4$, —$CONR^5R^6$, —$SO_2NR^7R^8$, —$C(=O)R^{13}$, —$XC(=O)R^{13}$, phenyl and monocyclic heteroaryl, wherein said heteroaryl is selected from five to seven membered aromatic rings containing from one to four heteroatoms selected from oxygen, nitrogen and sulfur, and wherein A, D, $R^4$, $R^5$, $R^6$, $R^7$, $R^8$ and $R^{13}$ are defined above. In a particular embodiment, $R^2$ and $R^3$, together with the ABCD ring of formula II, form a bicyclic or tricyclic ring system. In a further embodiment, one or both of $R^2$ and $R^3$ are —$C(=O)R^{13}$ wherein $R^{13}$ is $(C_1-C_6)$alkyl. In yet another embodiment, one of $R^2$ and $R^3$ is —$COR^{13}$ wherein $R^{13}$ is $(C_1-C_6)$alkyl or $(C_1-C_3)$alkyl optionally substituted with from one to seven fluorine atoms. In another embodiment, one of $R^2$ and $R^3$ is $CF_3$, fluoro, cyano, $(C_2-C_6)$ alkynyl or $C_2F_5$.

The present invention also provides the compound of formula II, wherein $R^2$ and $R^3$, together with the ABCD ring of formula II, form a bicyclic ring system selected from the following:

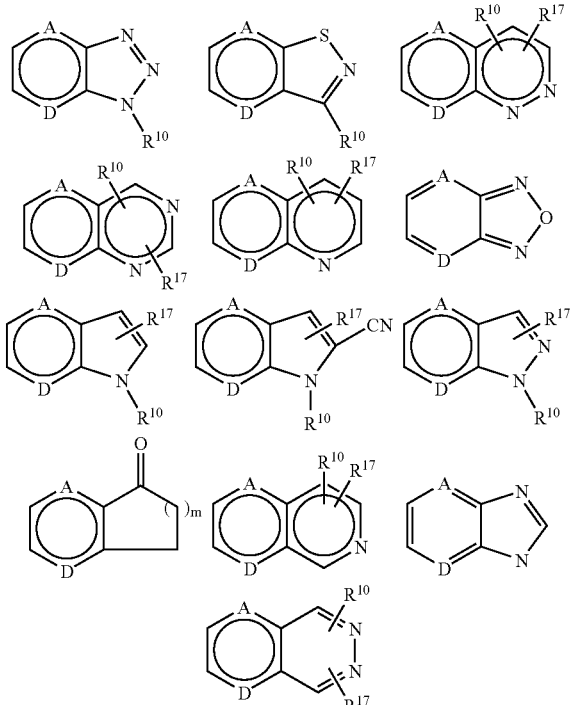

wherein A, D, $R^{10}$ and $R^{17}$ are defined above, and m is zero, one or two.

The present invention also provides the compound of formula III or IV, having a structure:

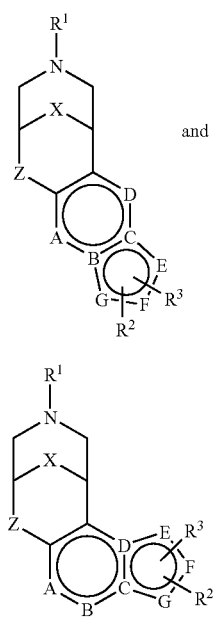

wherein E, F and G are independently C, N, O or S, with the proviso that (a) at least one of E, F and G is N, O or S, (b) no adjacent pair thereof consists solely of O, and (c) E, F and G are not all S or N; wherein the dashed circle represents either an aromatic ring, one isolated double bond, two or three double bonds, either conjugated or unconjugated, or a fully saturated ring; and wherein A, B, C, D, $R^1$, $R^2$, $R^3$ and X are defined above. In one embodiment, X is methylene or ethylene. In another embodiment, $R^1$ is hydrogen, methyl or benzyl. In a further embodiment, $R^2$ and $R^3$ are independently hydrogen or methyl.

The present invention also provides the compound of formula V or VI, having a structure:

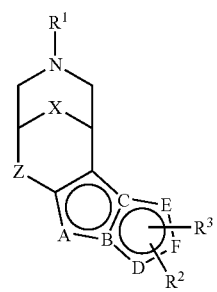

V

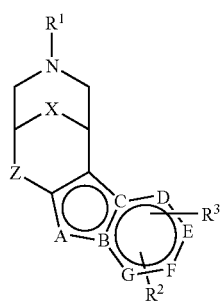

VI wherein E, F and G are independently C, N, O or S, with the proviso that (a) at least one of E, F and G is N, O or S, (b) no adjacent pair thereof consists solely of O, and (c) E, F and G are not all S or N; wherein the dashed circle represents either an aromatic ring, one isolated double bond, two or three double bonds, either conjugated or unconjugated, or a fully saturated ring; and wherein A, B, C, D, $R^1$, $R^2$, $R^3$ and X are defined as above. In one embodiment, $R^1$ is hydrogen, methyl or benzyl. In another embodiment, $R^2$ and $R^3$ are independently hydrogen or methyl.

Specific examples of compounds of the invention are:
(+)-4,10-diaza-tricyclo[6.3.1.0$^{2,7}$]dodeca-2(7),3,5-triene
(+)-3,11-diaza-tricyclo[7.3.1.0$^{2,7}$]trideca-2(7),3,5-triene
(+)-6,11-diaza-tricyclo[7.3.1.0$^{2,7}$]trideca-2(7),3,5-triene
(+)-4,11-diaza-tricyclo[7.3.1.0$^{2,7}$]trideca-2(7),3,5-triene
(+)-5,11-Diaza-tricyclo[7.3.1.02,7]trideca-2(7),3,5-triene
(+)-4-methyl-3,5,10-triaza-tricyclo[6.3.1.0$^{2,7}$]dodeca-2(7),3,5-triene
(+)-3,5,10-triaza-tricyclo[6.3.1.0$^{2,7}$]dodeca-2(7),3,5-trien-4-ylamine
(+)-11-methyl-3,11-diaza-tricyclo[7.3.1.0$^{2,7}$]trideca-2(7),3,5-triene
(+)-5,11-diaza-tricyclo[7.3.1.0$^{2,7}$]trideca-2(7),3-dien-6-one
(+)-6-methoxy-5,11-diaza-tricyclo[7.3.1.0$^{2,7}$]trideca-2(7),3,5-triene (+)-5-methyl-5,11-diaza-tricyclo[7.3.1.0²,⁷]trideca-2(7),3-dien-6-one
(+)-3-tert-butyl-3,4,9-triaza-tricyclo[5.3.1.0²,⁶]undeca-2(6),4-diene
(+)-3,14-diazatetracyclo [10.3.1.0²,¹¹.0⁴,⁹]-hexadeca-2(11),3,5,7,9-pentane
(+)-3-pyridin-2-yl-3,4,9-triaza-tricyclo[5.3.1.0²,⁶]undeca-2(6),4-diene
(+)-4-phenyl-3,5,10-triaza-tricyclo[6.3.1.0²,⁷]dodeca-2(7),3,5-triene
(+)-4-pyridin-4-yl-3,5,10-triazatricyclo[6.3.1.0²,⁷]dodeca-2(7),3,5-triene
(+)-3-(4-fluoro-phenyl)-3,4,9-triaza-tricyclo[5.3.1.0²,⁶]undeca-2(6),4-diene
(+)-5,7-dibromo-3,14-Diazatetracyclo[10.3.1.0²,¹¹.0⁴,⁹]-14-benzyl-hexadeca-2(11),3,5,7,9-pentane
(+)-3,14-diazatetracyclo [10.3.1.0²,¹¹.0⁴,⁹]-hexadeca-2(11),3,5,7,9-pentane
(+)-isomers of the following compounds:

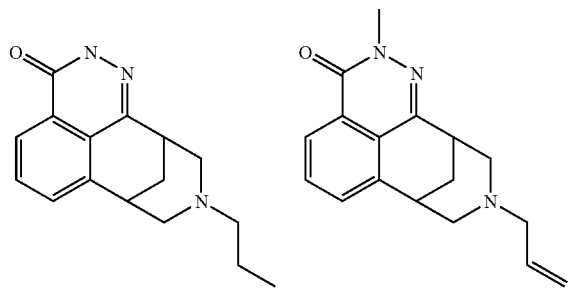

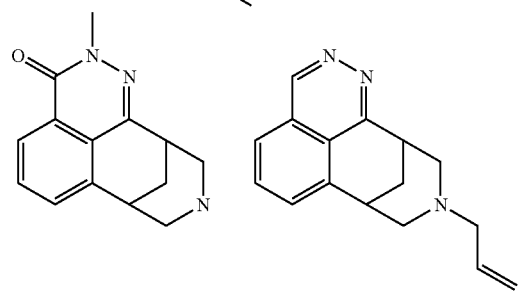

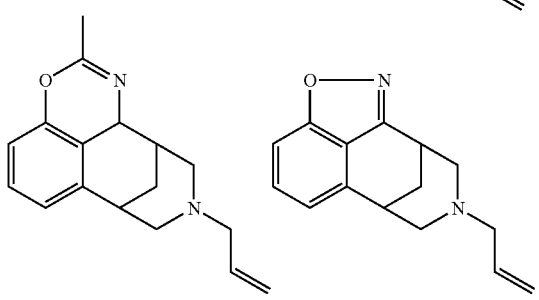

(−)-4,10-diaza-tricyclo[6.3.1.0²,⁷]dodeca-2(7),3,5-triene
(−)-3,11-diaza-tricyclo[7.3.1.0²,⁷]trideca-2(7),3,5-triene
(−)-6,11-diaza-tricyclo[7.3.1.0²,⁷]trideca-2(7),3,5-triene
(−)-4,11-diaza-tricyclo[7.3.1.0²,⁷]trideca-2(7),3,5-triene
(−)-5,11-Diaza-tricyclo[7.3.1,02,7]trideca-2(7),3,5-triene
(−)-4-methyl-3,5,10-triaza-tricyclo[6.3.1.0²,⁷]dodeca-2(7),3,5-triene
(−)-3,5,10-triaza-tricyclo[6.3.1.0²,⁷]dodeca-2(7),3,5-trien-4-ylamine
(−)-11-methyl-3,11-diaza-tricyclo[7.3.1.0²,⁷]trideca-2(7),3,5-triene
(−)-5,11-diaza-tricyclo[7.3.1.0²,⁷]trideca-2(7),3-dien-6-one
(−)-6-methoxy-5,11-diaza-tricyclo[7.3.1.0²,⁷]trideca-2(7),3,5-triene
(−)-5-methyl-5,11-diaza-tricyclo[7.3.1.0²,⁷]trideca-2(7),3-dien-6-one
(−)-3-tert-butyl-3,4,9-triaza-tricyclo[5.3.1.0²,⁶]undeca-2(6),4-diene
(−)-3,14-diazatetracyclo [10.3.1.0²,¹¹.0⁴,⁹]-hexadeca-2(11),3,5,7,9-pentane
(−)-3-pyridin-2-yl-3,4,9-triaza-tricyclo[5.3.1.0²,⁶]undeca-2(6),4-diene
(−)-4-phenyl-3,5,10-triaza-tricyclo[6.3.1.0²,⁷]dodeca-2(7),3,5-triene
(−)-4-pyridin-4-yl-3,5,10-triaza-tricyclo[6.3.1.0²,⁷]dodeca-2(7),3,5-triene
(−)-3-(4-fluoro-phenyl)-3,4,9-triaza-tricyclo[5.3.1.0²,⁶]undeca-2(6),4-diene
(−)-5,7-dibromo-3,14-Diazatetracyclo[10.3.1.0²,¹¹.0⁴,⁹]-14 benzyl-hexadeca-2(11),3,5,7,9-pentane
(−)-3,14-diazatetracyclo [10.3.1.0²,¹¹.0⁴,⁹]-hexadeca-2(11),3,5,7,9-pentane (−)-isomers of the following compounds:

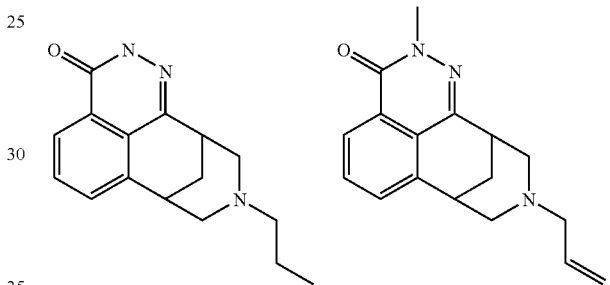

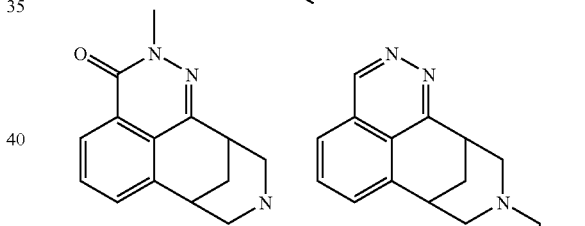

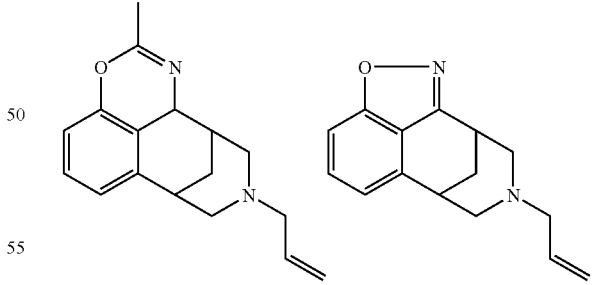

or a pharmaceutically acceptable salt thereof.

The compounds of the present invention may be used to bind to and modulate (i.e., inhibit, partially inhibit, activate, or partially activate) a nicotinic receptor or receptors in a mammal, including a human. The present compounds exhibit pharmacological activity consistent with such binding. Compounds according to the present invention may also be used as reference materials, reference standards, including calibration standards and as synthetic intermediates.

The present invention also relates to all radiolabeled forms of the compounds of the formulas I–VI. Preferred radiolabeled compounds of formulas I–VI are those wherein the radiolabels are selected from as $^3H$, $^{11}C$, $^{14}C$, $^{18}F$, $^{123}I$ and $^{125}I$. Such radiolabeled compounds are useful as research and diagnostic tools in metabolism studies, such as pharmacokinetics studies, etc., and in binding assays in both animals and man.

The present invention also relates to a pharmaceutical composition for use in reducing nicotine addiction or aiding in the cessation or lessening of tobacco use in a mammal, including a human, comprising an amount of a compound of the formula I–VI, or a pharmaceutically acceptable salt thereof, that is effective in reducing nicotine addiction or aiding in the cessation or lessening of tobacco use and a pharmaceutically acceptable carrier.

The present invention also relates to a method for reducing nicotine addiction or aiding in the cessation or lessening of tobacco use in a mammal, including a human, comprising administering to said mammal an amount of a compound of the formula I–VI, or a pharmaceutically acceptable salt thereof, that is effective in reducing nicotine addiction or aiding in the cessation or lessening of tobacco use.

The present invention also relates to a method of treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD), attention deficit disorder (ADD), restless legs syndrome (RLS), mild cognitive impairment, cognitive enhancement in schizophrenia, drug induced extrapyramidal symptoms, conduct disorder, oppositional defined disorder, anxiety in anxious smokers, cardiovascular risk in pregnancy, delayed ejaculation, emesis, symptoms due to injury inflicted by biological warfare, diarrhea, nicotine gum addiction, sleep prevention, ischemia, and Tourette's Syndrome in a mammal, comprising administering to a mammal in need of such treatment an amount of a compound of the formula I–VI, or a pharmaceutically acceptable salt thereof, that is effective in treating such disorder or condition.

The present invention also relates to a pharmaceutical composition for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (, dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD), attention deficit disorder (ADD), restless legs syndrome (RLS), mild cognitive impairment, cognitive enhancement in schizophrenia, drug induced extrapyramidal symptoms, conduct disorder, oppositional defined disorder, anxiety in anxious smokers, cardiovascular risk in pregnancy, delayed ejaculation, emesis, symptoms due to injury inflicted by biological warfare, diarrhea, nicotine gum addiction, sleep prevention, ischemia, and Tourette's Syndrome in a mammal, comprising an amount of a compound of the invention, or a pharmaceutically acceptable salt thereof, and a pharmaceutically acceptable carrier. The invention is also useful for enhancing smell and taste, for the secondary prevention of cancer, for aiding craving withdrawal and blockade reward, as an angiogenesis stimulator, for aiding induction of cessation for smoking, for aiding induction of cessation for addiction, as well as for the long-term maintenance of an addiction-free state, and reducing prolactin in pituitary adenoma.

This invention also relates to the pharmaceutically acceptable acid addition salts of the compounds of the invention. Examples of pharmaceutically acceptable acid addition salts of the compounds of the invention are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malic acid, di-p-toluoyl tartaric acid, and mandelic acid, as well salts formed from other acids known to those of skill in the art to form pharmaceutically acceptable acid addition salts to basic compounds. Other possible acid addition salts are, e.g., salts containing pharmaceutically acceptable anions, such as the hydroiodide, nitrate, sulfate or bisulfate, phosphate or acid phosphate, acetate, lactate, gluconate, saccharate, benzoate, methanesulfonate, ethanesulfonate, benzenesulfonate, and pamoate (i.e., 1.1'-methylene-bis-(2-hydroxy-3-naphthoate) salts).

Unless otherwise indicated, the term "halo", as used herein, includes fluoro, chloro, bromo and iodo.

Unless otherwise indicated, the term "alkyl", as used herein, includes straight chain moieties, and where the number of carbon atoms suffices, branched and cyclic moieties.

The term "alkoxy", as used herein, means "—O-alkyl" or "alkyl-O—", wherein "alkyl" is defined as above.

The term "alkylene, as used herein, means an alkyl radical having two available bonding sites (i.e.,-alkyl-), wherein "alkyl" is defined as above.

Unless otherwise indicated, the term "one or more substituents", as used herein, refers to from one to the maximum number of substituents possible based on the number of available bonding sites.

The term "alkyl", as used herein, unless otherwise indicated, includes saturated monovalent hydrocarbon radicals having straight, cyclic or branched moieties. Examples of alkyl groups include, but are not limited to, methyl, ethyl, propyl, isopropyl, sec-butyl and t-butyl. Within context, the use of the term "alkyl" may also subsume the use of or refer to alkylene groups, i.e., a hydrocarbon radical derived from alkyl groups which are diradicals, rather than monoradicals.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl.

The term "carbocyclic", as used herein, unless otherwise indicated, refers to a cyclic group in which all of the atoms of the ring are carbon atoms. Representative carbocyclic groups include cycloalkyl groups as described above. The term carbocyclic subsumes the term aryl within it.

The term "heterocyclic", as used herein, unless otherwise indicated, refers to a cyclic group in which at least one atom of the ring is a heteroatom (i.e., O, S or N). The term heterocyclic subsumes the term heteroaryl within it. Thus, a 5- to 7-membered heterocyclic group subsumes a 5- to 7-membered heteroaryl group within it.

The term "aryl", as used herein, unless otherwise indicated, includes an organic radical derived from an aromatic hydrocarbon by removal of one hydrogen, such as phenyl, naphthyl, indenyl, and fluorenyl.

The term "heteroaryl", as used herein, refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridone, hydantoin, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. The foregoing groups, as derived from the compounds listed above, may be C-attached or N-attached where such is possible. For instance, a group derived from pyrrole may be pyrrol-1-yl (N-attached), pyrrol-2-yl or pyrrol-3-yl (C-attached). The terms referring to the groups also encompass all possible tautomers.

The term "phenyl-fused" or "heteroaryl-fused", as used herein, refers to a heterocyclic or carbocyclic group which forms a ring by attaching or bonding two atoms (carbon and/or heteroatoms) of the heterocyclic or carbocyclic group to two carbon atoms of the phenyl group. The term "reductive amination", as used herein, refers to any process whereby the combination of an aldehyde or a ketone, or aldehyde or ketone equivalent, such as a bisulfite addition complex of an aldehyde, is combined with, in reference to the subject invention, a primary amine, secondary amine or ammonia, or ammonia source, such that the compounds condense to generate an intermediate imine or iminium ion that may be subjected to reduction by means of hydrogenation, such as mediated by a metal species such as palladium or platinum in many forms useful for reduction and a hydrogen source, such as hydrogen gas, or any precursor to hydrogen gas, including but not limited to formate derivatives or cyclohexadiene, or other hydride sources whereby hydride delivery from said source occurs by mechanisms commonly understood and employed. These include hydride reagents such as boron or aluminum hydride sources, for instance borohydrides, such as $[(X)_n BH_{4-n}]^-$ (n=0, 1, 2, 3) or aluminum hydrides such as $[(X)_n AlH_{4-n}]^-$ (n=0, 1, 2, 3) (wherein X may be any of the commonly cited ligands for transformations such a reductive amination including but not limited to acetoxy, trifluoroacetoxy, alkoxy, or lower alkyl for boron or alkoxy or lower alkyl for aluminum). Other hydrides may be equally suited to these transformations (for instance silanes or stannanes).

The term "reducing" or "reductive conditions", as used herein, refers to any process whereby dehydrohalogenation, hydrogenolysis, hydrogenation, or reduction of unsaturated bonds occurs as desired.

The term "leaving group", as used herein, refers to any group suitable in the conversion of a primary amine, secondary amine or ammonia or ammonia source that effectively departs in a bond-forming event from a carbon atom of interest, such as in an alkylation reaction. Suitable groups include halides (iodide, bromide or chloride), sulfonates (such methane sulfonate, trifluoromethanesulfonate or aryl sulfonates such as tosyl or nosyl groups), epoxides or aziridines or any variation that is well known to those of skill in the art. In addition, the processes involving leaving groups may be employed in the formation of other C—X bonds where the nucleophile X is oxygen, sulfur or carbon centered.

The compounds of formulas I–VI may have optical centers and therefore may occur in different enantiomeric configurations. The invention includes all enantiomers, diastereomers, and other stereoisomers of compounds of formulas I–VI, as well as racemic and other mixtures thereof.

The term "compound", as used herein, unless otherwise indicated, refers to any specific chemical compound disclosed herein. Within its use in context, the term generally refers to a single compound, but in certain instances may also refer to stereoisomers and/or optical isomers (including racemic mixtures), as well as specific enantiomers or enantiomerically enriched mixtures of disclosed compounds.

The term "effective" is used herein, unless otherwise indicated, to describe an amount of a compound which, in context, is used to produce or effect an intended result, whether that result relates to the treatment of a disease state, disorder or condition or alternatively, is used to produce another compound, agent or composition.

The terms "treatment", "treating", and the like, refers to reversing, alleviating, or inhibiting the progress of the disorder or condition to which such term applies, or one or more symptoms of such disorder or condition. As used herein, these terms also encompass, depending on the condition of the patient, preventing the onset of a disorder or condition, or of symptoms associated with a disorder or condition, including reducing the severity of a disorder or condition or symptoms associated therewith prior to affliction with said disorder or condition. Thus, "treatment", as used herein, can refer to administration of a compound of the invention to a subject that is not at the time of administration afflicted with the disorder or condition. "Treating" thus also encompasses preventing the recurrence of a disorder or condition or of symptoms associated therewith.

The terms "treatment", "treating", and the like, when referred to with regard to chemical transformations, refers to the act of combining or mixing in a manner compatible with the desired admixing of materials stated in the experimental description or procedure.

The term "addiction", as used herein, for example in "drug addiction" and "alcohol addiction", unless otherwise indicated, refers to a maladaptive use of a substance, which may be either with physiological dependence or without. The term "addiction" thus includes both substance abuse (such as to nicotine or nicotine containing or producing substances such as tobacco) and substance dependence (such as to nicotine or nicotine containing or producing substances such as tobacco). The maladaptive pattern of substance use may manifest itself in recurrent and significant adverse consequences related to the repeated use of the substance. The recurrent substance use may result in adverse long-term health comsequences. The maladaptive use of a substance may involve continued use of the substance despite persistent negative health consequences. The maladaptive pattern of substance use may involve clinically significant impairment or distress, for example manifested by tolerance for the substance, withdrawal symptoms, unsuccessful efforts to cut down or control the substance use, and/or taking larger amounts of the substance and/or taking amounts of the substance over a longer period than was intended and self-injurious continued use of the substance. Substances to which an addiction may be formed include, but are not limited to nicotine and nicotine containing products.

References herein to disease states, disorders and conditions "mediated by a nicotinic receptor or receptors" indicate disorders or conditions the treatment of which can be facilitated by modulating (i.e. inhibiting, partially inhibiting, activating, or partially activating) a nicotinic receptor or receptors. Examples of disorders and conditions the treatment of which is facilitated by modulation of a nicotinic receptor or receptors include, but are not limited to, inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD), attention deficit disorder (ADD), restless legs syndrome (RLS), mild cognitive impairment, cognitive enhancement in schizophrenia, drug induced extrapyramidal symptoms, conduct disorder, oppositional defined disorder, anxiety in anxious smokers, cardiovascular risk in pregnancy, delayed ejaculation, emesis, symptoms due to injury inflicted by biological warfare, diarrhea, nicotine gum addiction, sleep prevention, ischemia, and Tourette's Syndrome.

DETAILED DESCRIPTION OF THE INVENTION

Compounds according to the subject invention, generally as depicted in formulas I–VI and as described more fully herein, and their pharmaceutically acceptable salts can be prepared according to the following reaction Schemes I through XI as described herein. Unless otherwise indicated $R^1$, $R^2$, $R^3$, X, Y, (Het)

and structural formulas I–VI are as defined generally above. Isolation and purification of the products is accomplished by standard procedures which are known to a chemist of ordinary skill in the art. In addition, by following the disclosed chemistry more generically and/or by analogy, one of ordinary skill may readily provide all of the compounds according to the subject invention.

As used herein, the expression "reaction inert solvent" refers to a solvent system in which the components do not interact with starting materials, reagents, or intermediates of products in a manner that adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene, *Protective Groups in Organic Chemistry*, John Wiley & Sons, 1981; and T. W. Greene and P. G. M. Wuts, *Protective Groups in Organic Chemistry*, John Wiley & Sons, 1991.

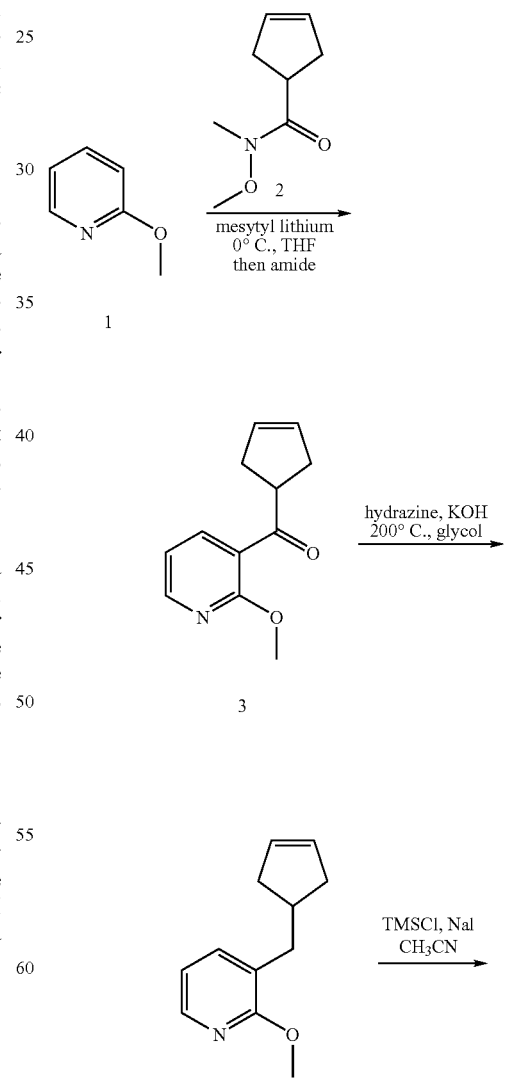

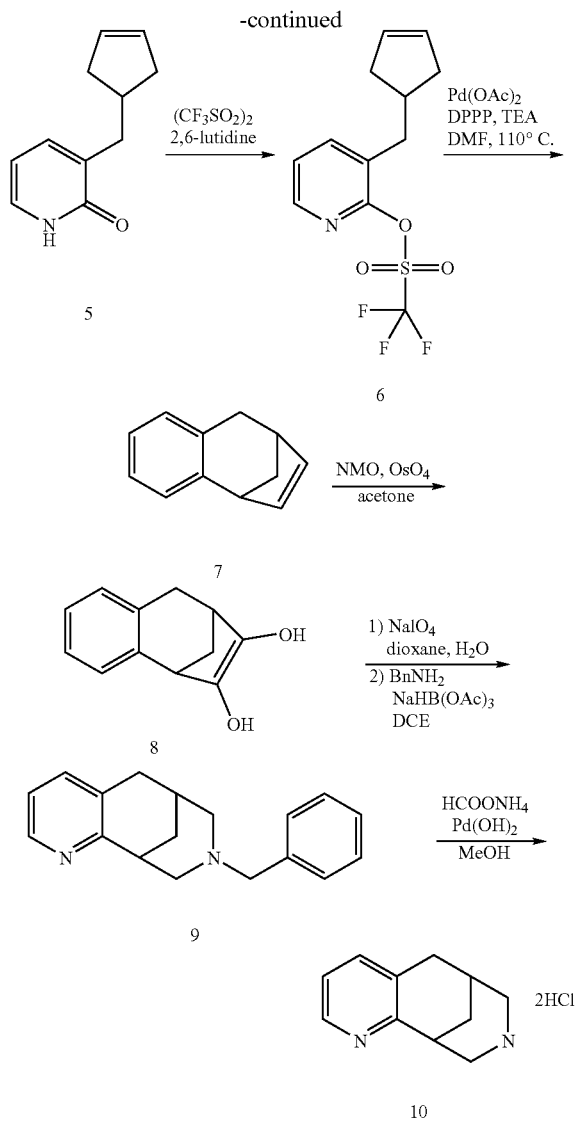

Referring to Scheme I, metalation of alkoxypyridines such as a compound of formula 1 by known methods (Comins, D. L.; LaMunyon, D. H. *Tetrahedron Lett.* 1988,29, 773–776) provides a method of regioselective preparation of ketones such as a compound of formula 3 as shown via reaction with a suitable amide such a compound of formula 2 (3-cyclopentylcarboxyamide). Reduction (Wolff-Kishner conditions), demethylation and conversion to trfluoromethanesulfonate ester provides a precursor suitable for Heck cyclization chemistry as described in U.S. Pat. No. 6,462,035. As such a standard Wolff-Kishner reduction of in situ generated or isolated keto-hydrazones (not shown) by the action of hydrazine in alcoholic solvent such as ethanol or glycol followed by reaction with sodium or potassium hydroxide at elevated temperature in a suitable solvent such as ethylene glycol, generally at 120–220° C., preferably at about 200° C., provides a compound of formula 4. Demethylation can be carried out with a suitable nucleophilic group such as halide including iodide or bromide. The reagent may be chosen from trimethylsilyl iodide, hydrogen iodide, TMS-Cl/NaI, hydrogen bromide, boron tribromide and the like. The reaction is typically carried out in an inert solvent such as dichloromethane, dichloroethane or toluene at ambient temperature up the reflux point of the solvent, preferably by the action of TMS-Cl/NaI in acetonitrile at 0° C. to the reflux temperature of the solvent, preferably at ambient temperature to provide a compound of formula 5. The compound of formula 5 may then be converted the trifluoromethanesulfonate ester 6 by the action of trifluoromethanesulfonic anhydride and a suitable base such as pyridine or 2,5-dimethylpyridine (lutidine) in a solvent such as dichloromethane, at temperatures ranging from −78° C. to the reflux temperature, preferably at −78 to 0° C. This is converted to a compound of formula 7 via standard Heck conditions. Methods to accomplish these transformations are described in U.S. Pat. No. 6,462,035 B1.

Again referring to Scheme I, a compound of the formula 7 may be prepared utilizing a "Heck cyclization reaction" through the action of a palladium catalyst such as tetrakis (triphenylphosphine)palladium, trans-benzyl(chloro)bis (triphenyl-phosphine)palladium(II), palladium on carbon, palladium acetate, palladium chloride, palladium trifluoroacetate, palladium trisdibenzylideneacetone, bis-(triphenylphoshine)palladium dichloride or other sources of coordinated palladium (0) or palladium (II). The reaction of 6 can be carried out in a solvent such as hexamethylphosphoramide (HMPA), N-methylpyrrolidone (NMP), ethanol, methanol, water or DMF, DMA, acetonitrile or other suitable solvents at temperatures from ambient to 130° C. for 6–48 hours at 1–2 atmospheres pressure. Alternatively palladium acetate or palladium trifluoroacetate in the presence of a ligand such as triphenylphosphine or tri-o-toluyl phosphine and with a quaternary ammonium salt such as tetrabutylammonium bromide, tetrabutylammonium chloride, tetrabutylammonium acetate in the presence of a base such as sodium acetate or potassium acetate and in a solvent such as DMF or dimethyl acetamide (DMA) may be effective. Alternatively the reaction may be performed without added salts, and by reaction with a secondary or tertiary amine base such as triethylamine. The reaction may be run at ambient temperature to the reflux point of the solvent. Often a degassed reaction solution is preferred as may be determined by one of skill in the art. A preferred condition includes reaction of a compound of formula 6 and palladium acetate, 1,3-bis(diphenylphosphino) propane and triethylamine in DMF at 100° C. for about 18 hours. These conditions provide a bicyclic olefinic compound such as 7 (for examples and further description of these methods see U.S. Pat. No. 6,462,035 B1). The olefin such as 7 may be converted by the appropriate methods to give the desired amine of formula I by a standard oxidative cleavage/reductive amination process (see Coe, J. W. *Organic Lett.* 2000, 2, 4205–4208). As such first this olefin is converted to its corresponding diol, a compound of formula 8, by a standard dihydroxylation procedure (VanRheenen, V.; Cha, D. Y.; Hartley, W. M. *Org. Synth.* 1988, Coll. Vol. 6, 342–348). Standard oxidative cleavage with NaIO$_4$ provides an intermediate dialdehyde (not shown) that may be condensed with ammonia or a primary amine and a reducing agent such as NaCNBH$_3$ or NaBH(OAc)$_3$ in a solvent such as dichloroethane or dichloromethane to provide a compound of formula 9 (see (Abdel-Magid, A. F.; Carson, K. G.; Harris, B. D.; Maryanoff, C. A.; Shah, R. D. *J. Org. Chem.* 1996, 61, 3849). If the desired product lacks a N-substituent, removal of the substituent may be accomplished by standard means based on the selection of the radical. For instance if the group is the benzyl group, its removal may be accomplished by standard reductive removal methods. Equally useful is a method of introduction of nitrogen lacking a radical by, after cleavage of the diol such as in compound 8 to an intermediate dialdehyde, introduction of ammonium hydroxide and treatment of the mixture with a suitable palladium hydrogenation catalyst such as palladium on carbon or palladium hydroxide. The entire mixture may be placed under hydrogen pressure of at least 1 to 10 atmospheres. In such a case the intermediate olefin such as 7 may be exposed to catalytic osmium tetroxide and trimethylamine N-oxide in anhydrous dichloromethane for 36 hours at room temperature followed by treatment with sodium periodate in a mixture of ethanol and water for two hours and finally reduction over palladium hydroxide and three atmospheres of hydrogen with an ammonia source such as ammonium hydroxide or benzylamine at room temperature for 16–72 hours to afford a compound of formula 10 directly.

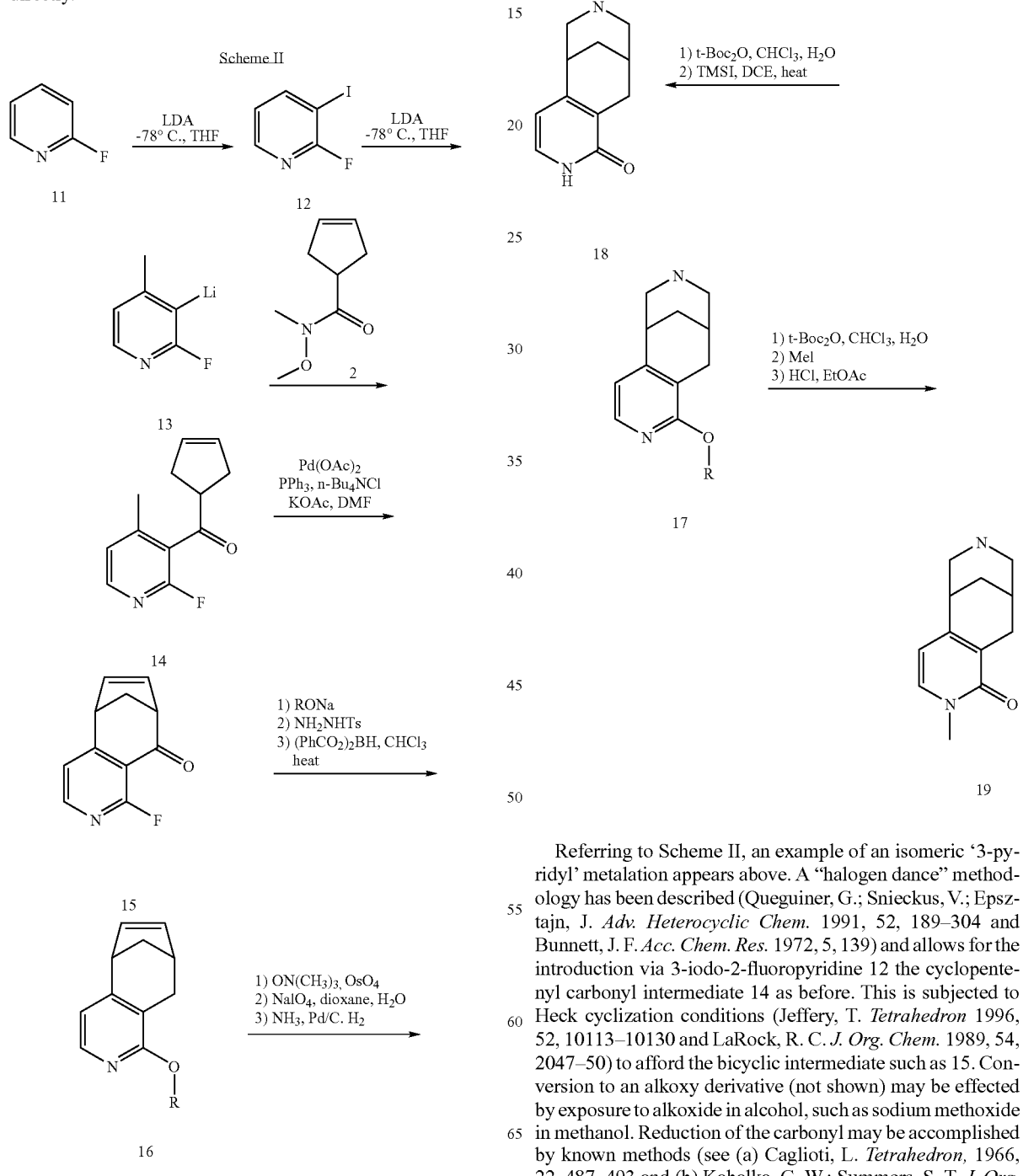

Referring to Scheme II, an example of an isomeric '3-pyridyl' metalation appears above. A "halogen dance" methodology has been described (Queguiner, G.; Snieckus, V.; Epsztajn, J. *Adv. Heterocyclic Chem.* 1991, 52, 189–304 and Bunnett, J. F. *Acc. Chem. Res.* 1972, 5, 139) and allows for the introduction via 3-iodo-2-fluoropyridine 12 the cyclopentenyl carbonyl intermediate 14 as before. This is subjected to Heck cyclization conditions (Jeffery, T. *Tetrahedron* 1996, 52, 10113–10130 and LaRock, R. C. *J. Org. Chem.* 1989, 54, 2047–50) to afford the bicyclic intermediate such as 15. Conversion to an alkoxy derivative (not shown) may be effected by exposure to alkoxide in alcohol, such as sodium methoxide in methanol. Reduction of the carbonyl may be accomplished by known methods (see (a) Caglioti, L. *Tetrahedron*, 1966, 22, 487–493 and (b) Kabalka, G. W.; Summers, S. T. *J. Org.*

Chem. 1981, 46, 1217–1218) to give a compound of formula 16. The conversion of the olefinic compound such as 16 to a piperidine such as 17 follows methods similar to those described above, and in particular similar to those described in the literature in a related synthesis (see, Coe, J. W. *Organic Lett.* 2000, 2, 4205–4208). This product of the general formulas I and II, a compound of formula 17, can be further converted if desired into the pyridone 18 by protection of the secondary nitrogen by standard methods such as with a t-butyl oxycarbonyl moiety followed by TMSI dealkylation of the alkyl ether, such as the methyl ether. This process also removes the t-butyl oxycarbonyl moiety to provide the pyridone 18. Alternatively t-butyl oxycarbonyl protected material may be converted to the N-alkyl pyridone moiety, by alkylation, with methyliodide for instance, followed by deprotection with for instance HCl under standard conditions it give a compound of the formula 19.

In each of the reactions discussed below, and as illustrated in Scheme II, above, pressure is not critical unless otherwise indicated. Pressures from about 0.5 atmospheres to about 5 atmospheres are generally acceptable, with ambient pressure, i.e., about 1 atmosphere, being preferred as a matter of convenience.

Referring to Scheme II, a compound of the formula 11 may be converted to compounds of the formula 12 by treatment with a suitable base such as lithium diisopropylamide, lithium bistrimethylsilylamide, potassium bistrimethylsilylamide, sodium bistrimethylsilylamide, lithium tetramethylpiperidide as well as bases such as n-butyl lithium, sec-butyl lithium, phenyl lithium and mesityl lithium. The reaction is carried out in an inert solvent such as tetrahydrofuran, ether, dimethoxyethane or dioxane and solvents such as toluene and hexane at a temperature between −78° C. and ambient temperature. Iodination may be conducted with solid iodine or solutions of iodine in anhydrous solvents. It may also be conducted with N-iodosuccinimide or iodine monochloride. The most preferred conditions use lithium diisopropylamide in THF at −78° C. and iodine. In a similar manner the related 3-bromo-2-fluoropyridine may be prepared by substituting bromine for iodine in the above sequence and may be used like the iodide in the preparation of compound 15.

Again referring to Scheme II above, a compound of the formula 14 may be prepared from 12 (or from 3-bromo-2-fluoropyridine) by treatment with a base such as lithium diisopropylamide, lithium bistrimethylsilylamide, potassium bistrimethylsilylamide, sodium bistrimethylsilylamide, lithium tetramethylpiperidide. The reaction is carried out in an inert solvent such as tetrahydrofuran, ether, dimethoxyethane or dioxane and solvents such as toluene and hexane at a temperature between −78° C. and ambient temperature. The resulting anion 13 which is formed through a "Halogen Dance" rearrangement is treated with an acylating agent such as cyclopent-3-enecarboxylic acid methoxymethylamide or formula 2 or cyclopent-3-enecarboxylic acid dimethylamide or cyclopent-3-enecarboxylic acid at a temperature between −78° C. and ambient temperature. The most preferred conditions involve formation of the anion 13 with lithium diisopropylamide and acylation with cyclopent-3-enecarboxylic acid methoxymethylamide 2 in THF at −78° C. If bromide is chosen to replace iodide in 12 then the product 14 will also have bromide in place of iodide. Either compound may be used in the synthesis of 15.

Again referring to Scheme II above, a compound of the formula 15 may be prepared utilizing a "Heck cyclization reaction" as described above referring to Scheme I. The most preferred conditions include reaction of a compound of formula 14 with palladium acetate and triphenylphosphine tetrabutylammonium bromide and potassium acetate in DMF at 100° C. for twenty minutes.

Again referring to Scheme II above, a compound of the formula 15 wherein the fluoride atom has been exchange for an alkoxy radical, can be prepared by reaction of 15 in a solvent such as methanol with a base such as sodium methoxide or potassium carbonate sodium hydroxide or sodium hydrogen carbonate. By choosing a different solvent and base other aliphatic and benzylic ethers may be prepared in a similar fashion. The most preferred conditions involve methanol as a solvent with sodium methoxide at the reflux point of the solvent.

Again referring to Scheme II above, a compound of the formula 16 may be prepared by a standard Wolff-Kishner reduction of keto-hydrazones with sodium or postassium hydroxide. Alternatively, the ketone may be converted to the tosylhydrazone by reaction of tosylhydrazine in refluxing ethanol. Reductive removal of the hydrazone may be carried out by reduction of the tosyl hydrazone with the adduct obtained by reaction of 2 equivalents benzoic acid and borane in THF or with catechol borane or by the reaction with potassium borohydride, sodium triacetoxyborohydride and sodium cyanoborohydride. This reduction can be carried out in a suitable inert solvent such as chloroform, dichloromethane, and dichloroethane at a temperature between −25° C. and ambient temperature. The solvent is removed and the residue is resuspended in a high boiling solvent such as ethylene glycol and treated with a suitable base such as potassium or sodium carbonate and heated to 100° C. The preferred conditions include formation of the tosylhydrazone with tosylhydrazine in refluxing ethanol followed by reduction of the tosylhydrazone with dibenzoylborane in alcohol free chloroform at 0° C. The final stage of the reduction is carried out in ethylene glycol with potassium carbonate heated to 100° C.

Again referring to Scheme II above, a compound of the formula 17 may be prepared by reaction of 16 with osmium tetroxide or potassium permanganate to afford a diol. Specifically, if osmium tetroxide is used in catalytic amounts, then a reoxidant is needed. Suitable reoxidants are N-methylmorpholine N-oxide, trimethylamine N-oxide, and sodium periodate. The reacton is typically run in an inert solvent such as dichloromethane, THF, dioxane or other suitable inert solvents at a temperature from 0° C. to ambient using a reaction time of 1 to 48 hours. The diol thus formed above is treated with sodium periodate or tetrabutyl ammonium periodate in ethanol or methanol in the presence of water at room temperature for a period of 1–12 hours. This was followed by the introduction of ammonium hydroxide and the mixture was treated with a suitable palladium hydrogenation catalyst such as palladium on carbon or palladium hydroxide. The entire mixture may then be placed under hydrogen pressure of at least 1 to 10 atmospheres. The most preferred conditions involve catalytic osmium tetroxide and trimethylamine N-oxide in anhydrous dichloromethane for 36 hours at room temperature followed by treatment with sodium periodate in ethanol water for two hours and finally reduction over palladium hydroxide and three atm of hydrogen at room temperature for 16 hours to afford a compound of formula 17.

Again referring to Scheme II above, nitrogen protection of 17 may be completed with CBz-chloride in a suitable solvent or mixture of solvents and base. Typical solvents include dichloromethane, chloroform, dichloroethane, toluene and water or a mixture of these with water. Suitable bases include sodium carbonate or sodium bicarbonate, triethylamine or diisopropylethylamine. The t-Boc group can be introduced using a reagent such as di-t-butyldicarbonate, di-t-butylpyrocarbonate, 2-(t-butoxycarbonyloxyimino)-2-phenylacetonitrile (t-Boc-ON), t-Boc-azide, t-Boc-chloride, t-Boc-fluoride and 2-(t-butoxycarbonyloxy)phthalimide or similar reagents wherein t-Boc refers to the residue tertiary butoxycarbonyl a useful protecting group. The reaction is conducted in a suitable solvent or mixture of solvents, including, but not limited to the following: dichloromethane, ethyl acetate, chloroform, benzene, toluene, ether, tetrahydrofuran (THF), dichloroethane and water with a suitable base including, but not limited to, the following: sodium, lithium and potassium carbonates, bicarbonates and hydroxides, imidazole, dimethylaminopyridine and trialkylamines such as triethylamine. The reaction requires 0.5 to 24 hours for completion. The temperature is not critical, the reaction being run between room temperature and the reflux temperature of the solvent or mixture of solvents. The reaction is generally run at a pressure between 0.5 and 2.0 atmospheres, preferably at atmospheric pressure. It is preferably carried out at reflux for 1–2 hours with t-Boc dicarbonate in a mixture of dichloromethane and water with sodium bicarbonate as base. The t-Boc protecting group can be readily removed from the protected products described above, to form the free amine compound by treatment with an acid such as hydrochloric, sulfuric, trifluoroacetic, acetic, nitric, hydrofluoric, hydrobromic and hydroiodic using water as a solvent or co-solvent or in anhydrous organic solvents such as methanol, ethanol, ether, ethyl acetate, dichloromethane and chloroform or mixtures thereof. The product is obtained as its acid salt which may be then treated with a suitable base including, but not limited to, the following: sodium, lithium and potassium carbonates, bicarbonates and hydroxides, generally, in water to afford the desired material as the free base form.

Again referring to Scheme II above, a compound of the formula 18 may be prepared through simultaneous or sequential deprotection of the O-methyl and t-Boc groups. O-Demethylation can be carried out with a suitable nucleophilic group such as halide including iodide or bromide. The reagent may be chosen from trimethylsilyl iodide, hydrogen iodide, TMS-Cl/NaI, hydrogen bromide, boron tribromide and the like. The reaction is typically carried out in an inert solvent such as dichloromethane, dichloroethane or toluene at ambient temperature up the reflux point of the solvent. Alternatively, reaction with methyl iodide affords an N-methylated compound 19 with simultaneous cleavage of the O-methyl. The preferred conditions for preparation of compounds of formula 18 involve trimethylsilyl iodide in dichloroethane at reflux for 2 hours. Reaction with methyl iodide is preferably carried out in a sealed tube at 130° C. for 4 hours to afford compounds such as 19 after t-Boc deprotection.

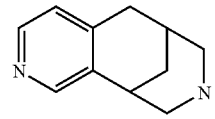

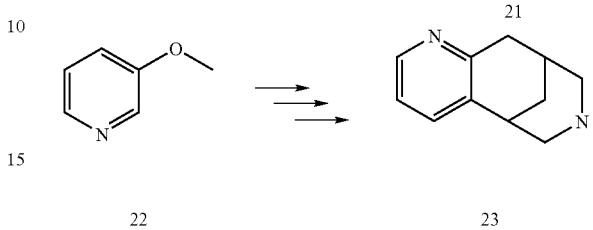

Referring to Scheme III, conditions as described in Schemes I and II may be applied to the preparation of additional isomers via regioselective metalation strategies of suitably substituted pyridines (Winkle, M. R.; Ronald, R. C. *J. Org. Chem.* 1982, 46, 2101–2108 and Comins, D. L.; LaMunyon, D. H. *Tetrahedron Lett.* 1988, 29, 773–776). Following methods described therein and generally described in Scheme I and II allows for ready access to compounds of formula 21 and 23, if for example one of skill in the art began with compounds of formula 20 and 22 respectively.

Scheme IV

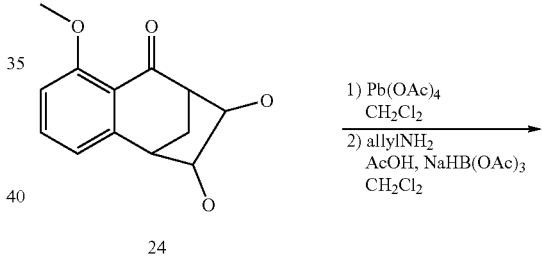

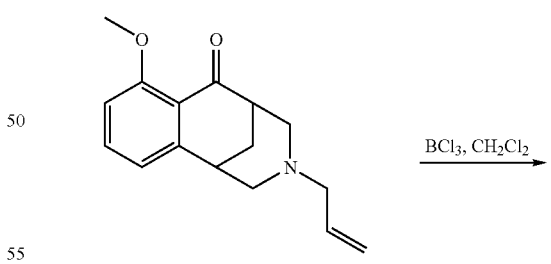

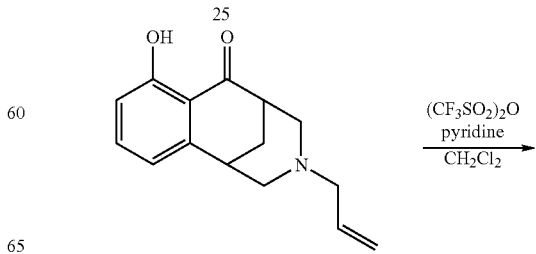

Scheme III

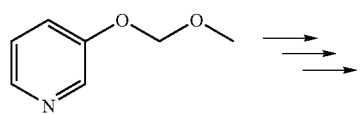

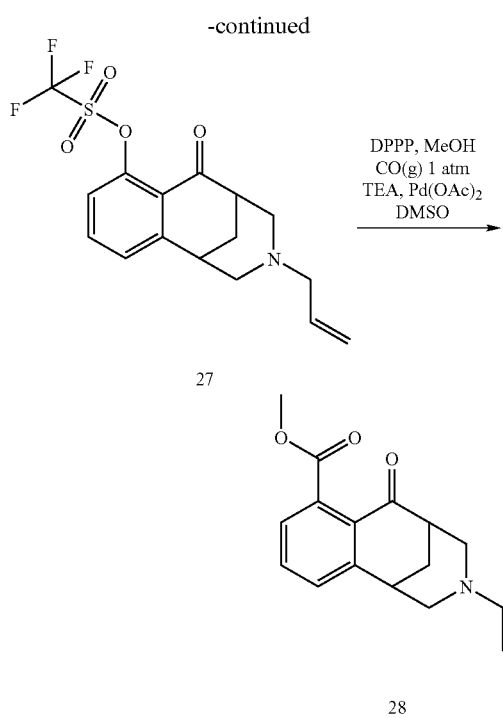

Referring to Scheme IV, a compound of formula 24, may be converted to the corresponding amine of formula 25 as depicted above utilizing lead tetraacetate, an alternative reagent for oxidative cleavage, or by methods more fully described in Schemes I and II above and in the Examples section. Demethylation can be carried out with a suitable nucleophilic group such as halide including iodide or bromide. The reagent may be chosen from trimethylsilyl iodide, hydrogen iodide, TMS-Cl/NaI, hydrogen bromide, boron tribromide and the like. The reaction is typically carried out in an inert solvent such as dichloromethane, dichloroethane or toluene at ambient temperature up the reflux point of the solvent. The preferred conditions for preparation of compounds of formula 25 to the phenol 26 is by the action of $BCl_3$ in a solvent such as dichloromethane, at temperatures ranging from −78° C. to reflux temperature, preferably at −78 to 0° C. The compound of formula 26 may then be converted to a keto-ester 28 by first activation as the trifluoromethanesulfonate ester 27 by the action of trifluoromethanesulfonic anhydride and a suitable base such as pyridine in a solvent such as dichloromethane, at temperatures ranging from −78° C. to the reflux temperature, preferably at −78 to 0° C. This is converted to a keto-ester via standard Heck carbonylation conditions (for instance see, Dolle, R. E.; Schmidt, S. J.; Kruse, L. I. *J. Chem. Soc., Chem. Commun.* 1987, 904–905). Methods to accomplish these transformations are also described in U.S. Pat. No. 6,462,035 B1.

Scheme V

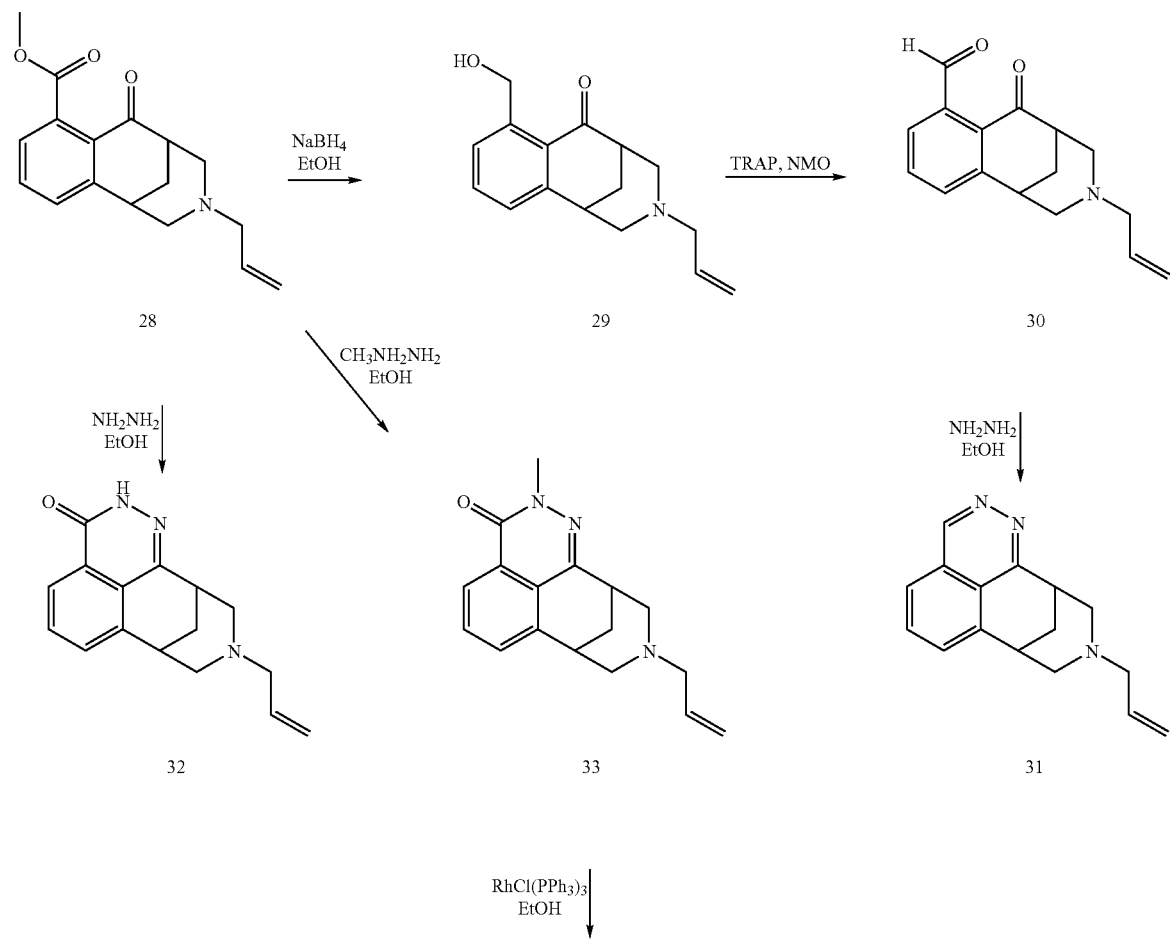

-continued

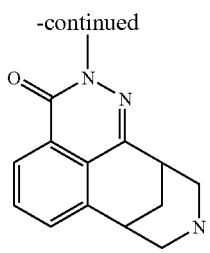

34

Referring to Scheme V, the keto-ester 28 may be converted by the action of NaBH$_4$ to an intermediate diol 29 that is readily oxidized by standard protocols, such as the catalytic ruthenium based TPAP (tetrapropylammonium perruthenate)/N-methylmorpholine N-oxide reagent system, to the intermediate keto-aldehyde 30 (see Ley, S. L. *Synthesis* 1994, 639 and *Aldrichinica Acta* 1990, 23, 13). Treatment of a compound of formula 30 with hydrazine in alcohol, preferably ethanol, at ambient temperature provides a useful preparation of a phthalazine compound of formula 31. Products such as this may be utilized as described in this invention as such or converted by standard means to the corresponding product lacking 1-alkyl substitution.

Again referring to Scheme V, treatment of the keto-ester 28 directly with hydrazine or mono-substituted hydrazine derivatives as one may desire, such as methyl hydrazine, in a solvent such as an alcohol, preferably ethanol, at a temperature such as ambient temperature, provides a condensation product derived from the loss of a molecule of water and a molecule of methanol. In the case of reactions with hydrazine itself, it is possible that the reduction of the allyl group, as is a known reductive action of hydrazine, may occur to provide the corresponding N-propyl derivative of formula 32. Other N-protective groups may be used to gain access to compound such as 32 lacking the protective group. The alkyl hydrazine derivative provides the 2-N-alkyl phthalazin-1-one of formula 33 regioselectively.

Again referring to Scheme V, removal of the allyl group, or other protecting group as may be incorporated as desired, can be accomplished under standard protocols, such as by the catalytic action of RuCl(PPh$_3$)$_3$ and a solvent such as ethanol. This is usually performed at the reflux temperature under conditions that allow for the removal of solvent and the so formed ethylallyl ether or other ether as determined by the alcohol of choice. Other standard methods for the removal of protecting groups are equally suitably, such as conditions employing palladium catalysis known in the art. This deprotection provides an effective method of preparation of a compound of formula 34.

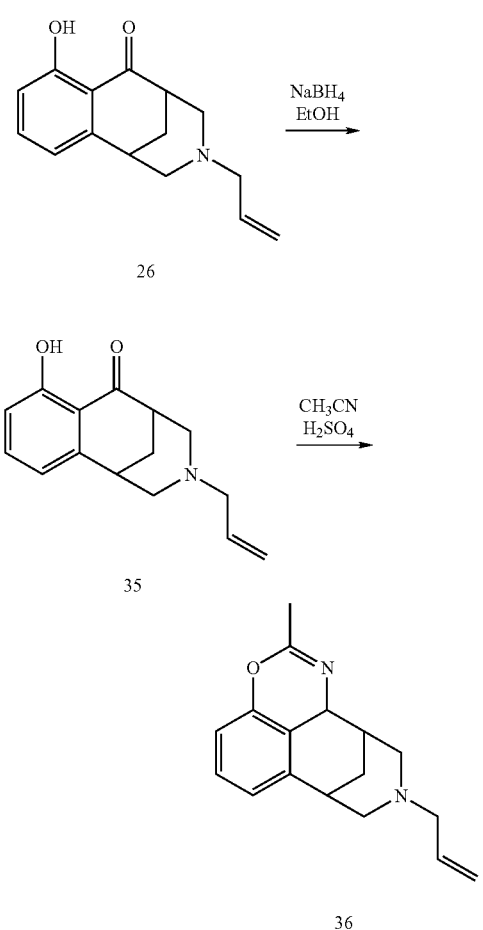

Referring to Scheme VI above, a phenolic-ketone of formula 26 may be reduced by, for instance, the action of NaBH$_4$ to provide a phenolic alcohol of formula 35 that is well suited to a Ritter reaction. This may for instance be used to provide the oxazine of formula 36 as depicted above. Under appropriate acidic conditions, such as upon exposure to mineral acids, for instance sulfuric acid, methane sulfonic acid or hydrochloric acid, preferably sulfuric acid, in the presence of alkyl or aryl nitrites, such as for instance acetonitrile, provides the corresponding oxazine. This is typically performed at a temperature that provides for reaction, such as at ambient temperature, but may require lower or elevated temperatures, depending upon the exact nature of the starting substrates involved.

Scheme VII

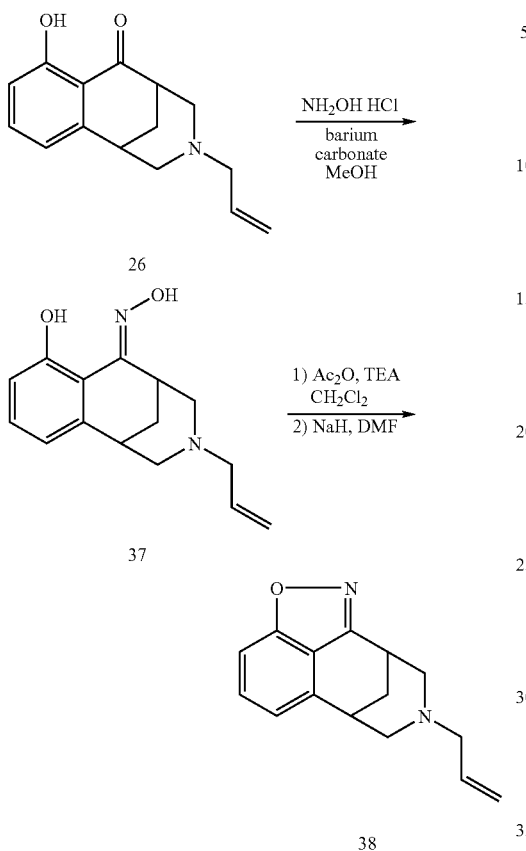

Scheme VIII

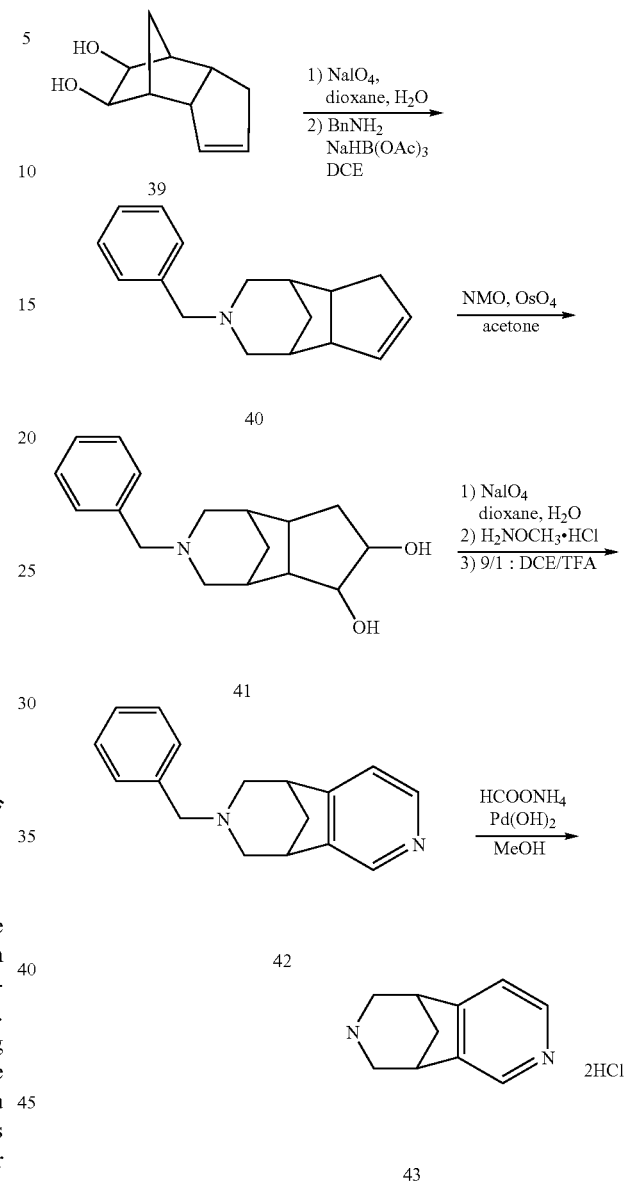

Referring to Scheme VII above, a compound such as the phenolic ketone 26 as depicted above is useful for conversion to the corresponding isoxazole of formula 38. This is typically performed via intermediate oximes of the formula 37. Oximes of this type are easily prepared by contacting hydroxylamine, or other equivalents, such as for instance O-sulfonyl hydroxylamines, and the keto-phenol of formula 26 under appropriate conditions, such as in an alcohol, such as methanol, in the absence or presence of a catalyst, such as for instance barium carbonate or other appropriate bases. This is performed at from room to the reflux temperature of the medium, preferably the reflux temperature. Once obtained, the oxime such as 37 may be activated, unless it was formed from a pre-activated species, such as for instance O-sulfonyl hydroxylamines, to give an intermediate suitable for closure to the tetracyclic ring system. This is done for instance by treatment with acetic anhydride to provide the O-acetyl oxime (not shown). This can be done with triethyl amine in an inert solvent such as dichloromethane at ambient temperature. This activated material may then be subjected to ring closing conditions, such as by exposure to base, for example NaH in a polar solvent such as a dipolar aprotic solvent such as DMF. This may be performed at any temperature that induces closure, for instance from 0° C. to the reflux temperature, preferably at room temperature. These conditions provide for the conversion to the desired isoxazole tetracylic such as a compound of formula 38.

Referring to Scheme VIII, dicyclopentadiene diol of formula 39 (3a,4,5,6,7,7a-hexahydro-1H-4,7-methano-indene-5,6-diol, see Freeman, F.; Kappos, J. C. J. Org. Chem. 1989, 54; 2730–2734) may be converted through a standard oxidative cleavage/reductive amination process as described hereinabove (Abdel-Magid, A. F.; Carson, K. G.; Harris, B. D.; Maryanoff, C. A.; Shah, R. D. J. Org. Chem. 1996, 61, 3849) to generate the piperidine of formula 40. The compound of formula 40 may be converted to its corresponding diol (not shown) by a standard dihydroxylation procedure (Van-Rheenen, V.; Cha, D. Y.; Hartley, W. M. Org. Synth. 1988, Coll. Vol. 6, 342–348) as described hereinabove to provide a diol of formula 41. The oxidation of olefins to the corresponding diols above may be accomplished by other standard means known to those of skill in the art, including for instance by the action of $KMnO_4$. Standard oxidative cleavage of 41 with for example $NaIO_4$ provides an intermediate dialdehyde (not shown). Equally useful, mineral or organic acid salts of a compound such as of formula 40 may be exposed in alcohol, for instance methanol, or water, to ozone. This will produce intermediate hydroperoxides, which may be reduced by exposure to suitable reductants such as dimethyl sulfide (methyl sulfide) to provide the intermediate dialdehyde salt directly. The intermediate dialdehyde is condensed with hydroxylamine or O-alkyl hydroxylamines to provide bisoximes (not shown). These are typically warmed in acid to provide the corresponding pyridine of formula 42. (For related methods see, Abood, L. G. *J. Am. Chem. Soc.* 1986, 108, 7864). Debenzylation by standard methods described above provides a compound of formula 43.

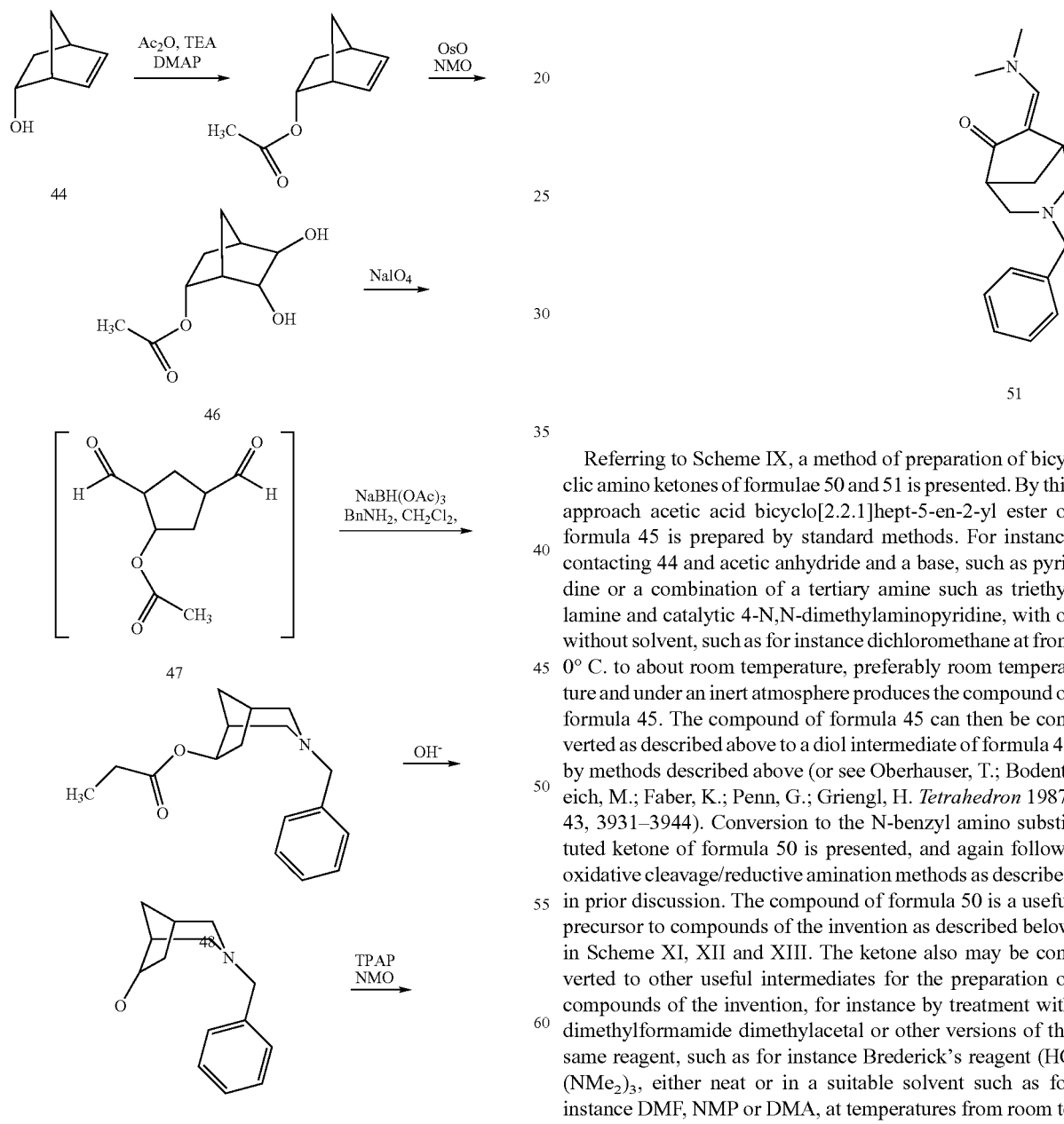

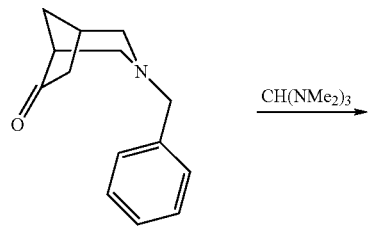

Referring to Scheme IX, a method of preparation of bicyclic amino ketones of formulae 50 and 51 is presented. By this approach acetic acid bicyclo[2.2.1]hept-5-en-2-yl ester of formula 45 is prepared by standard methods. For instance contacting 44 and acetic anhydride and a base, such as pyridine or a combination of a tertiary amine such as triethylamine and catalytic 4-N,N-dimethylaminopyridine, with or without solvent, such as for instance dichloromethane at from 0° C. to about room temperature, preferably room temperature and under an inert atmosphere produces the compound of formula 45. The compound of formula 45 can then be converted as described above to a diol intermediate of formula 46 by methods described above (or see Oberhauser, T.; Bodenteich, M.; Faber, K.; Penn, G.; Griengl, H. *Tetrahedron* 1987, 43, 3931–3944). Conversion to the N-benzyl amino substituted ketone of formula 50 is presented, and again follows oxidative cleavage/reductive amination methods as described in prior discussion. The compound of formula 50 is a useful precursor to compounds of the invention as described below in Scheme XI, XII and XIII. The ketone also may be converted to other useful intermediates for the preparation of compounds of the invention, for instance by treatment with dimethylformamide dimethylacetal or other versions of the same reagent, such as for instance Brederick's reagent (HC(NMe$_2$)$_3$, either neat or in a suitable solvent such as for instance DMF, NMP or DMA, at temperatures from room to 150° C. preferably at 100° C., provides a method of conversion to the dimethylaminomethylene bicyclic ketone of formula 51.

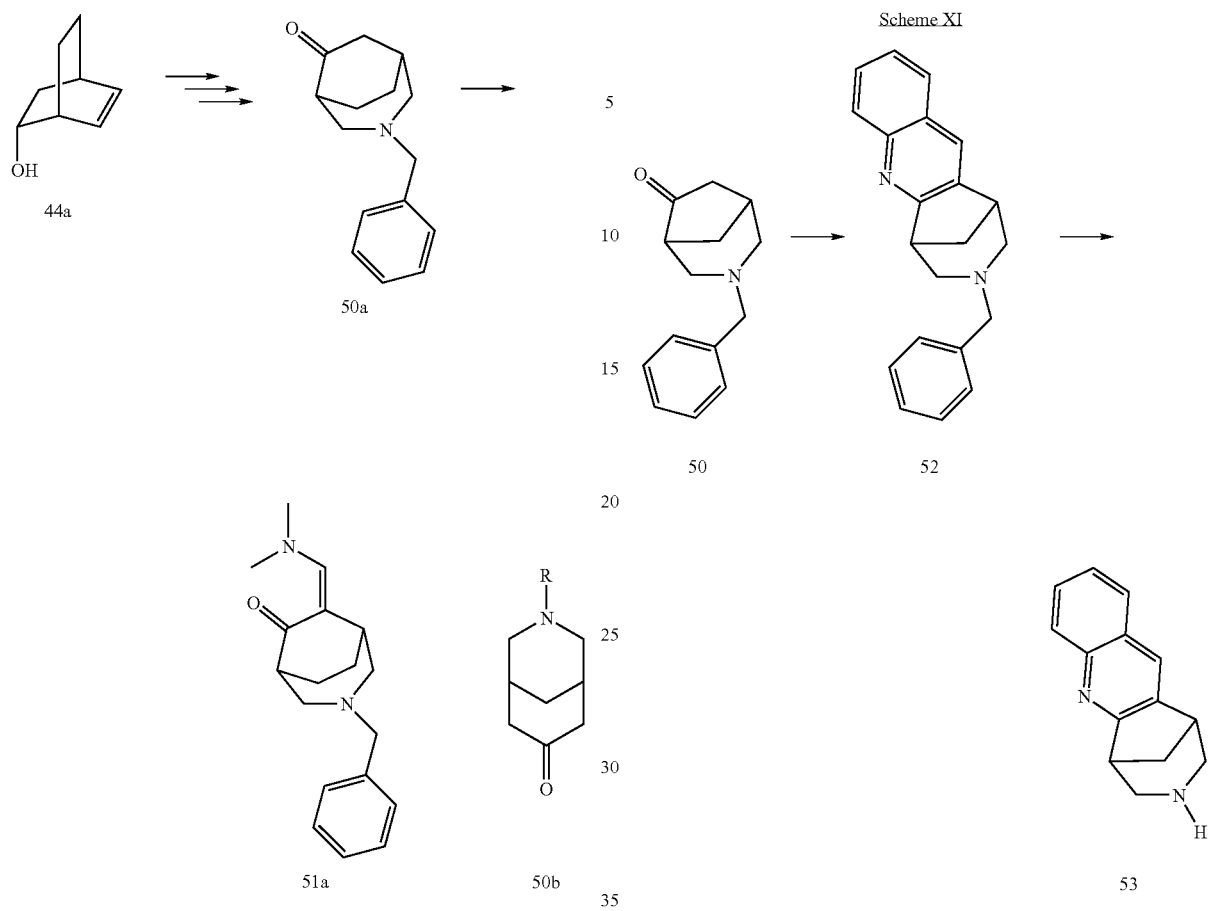

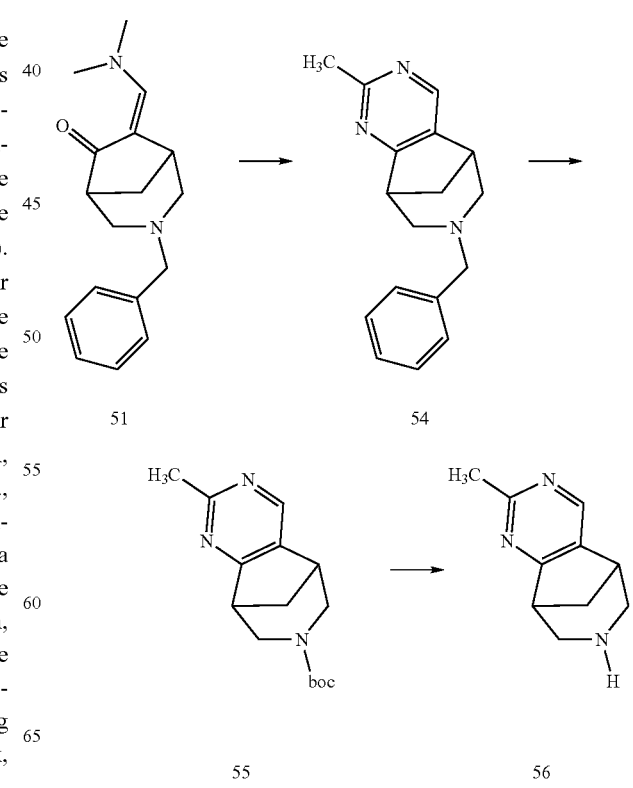

Referring to Scheme X, the chemistry above allows for the preparation of the homologous ketone of formula 50a. As such access to ketone 50a is possible from bicyclo[2.2.2]oct-5-en-2-ol (see *J. Org. Chem.* 1954, 19, 381–384), the compound of formula 44a, by the methods described in Scheme IX. Alternative methods of preparation of ketone 50a have been demonstrated (see *J. Org. Chem.* 1968, 33, 3195–3201). Analogously, the ketone 50a also may be converted to other useful intermediates for the preparation of compounds of the invention, for instance by treatment with dimethylformamide dimethylacetal or other versions of the same reagent, such as for instance Brederick's reagent (HC(NMe$_2$)$_3$, either neat or in a suitable solvent such as for instance DMF, NMP or DMA, at temperatures from room to 150° C. preferably at 100° C., provides a method of conversion to the dimethylaminomethylene bicyclic ketone of formula 51a. The ketones of formula 50a and 51a allow for the preparation of compounds of the invention wherein X is CH$_2$CH$_2$. In an analogous fashion, these conversions may be carried out on the related ketone whereby Z is CH$_2$ to give products of formulas I–VI ultimately so derived. Ketone 50b provides a useful starting material for these products of the invention (see Reints Bok, T.; Speckamp, W. H.; *Tetrahedron* 1979, 35, 267–272).

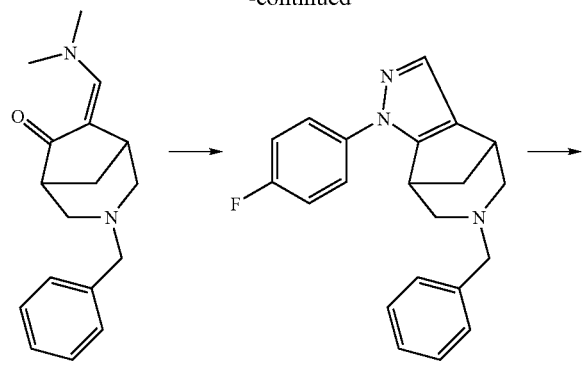

51

57

58

Referring to Scheme XI, standard methods of heteroaryl synthesis are applicable to the preparation of compounds of formula I–IV, for example a compound of formula 53. Friedlander synthesis may be applied to prepare quinoline-like structures (see for conditions Cheng, C. C.; Yan, S. J. in *Organic* Reactions 28, 37, 1982 and the examples section) from a compound of formula 50, 50a or 50b (for brevity only 50 is depicted). Fischer indole synthesis provides a method of preparation of indoles of formulas V–VI (see B. Robinson, *The Fischer Indole Synthesis* Wiley, New York, 1982). Conversion of the dimethylaminomethylene bicyclic ketone of formula 51 to compounds of the invention of formulas I–VI follows well-established methods involving condensation with urea, amidines, guanidines and hydrazines. Preparation of pyridines may be accomplished by well established means as described in *J. Org. Chem.* 2001, 60, 4194.

Again referring to Scheme XI, ketone of formula 50 in a suitable solvent such as acetic acid and catalyst such as sulfuric acid is treated with 2-amino benzaldehyde, or substituted carbocyclic or heterocyclic variants thereof. The mixture may be heated to 100° C. for up to 7 days, typically for 60 hours to provide a compound of formula 52. The benzyl-protecting group is removed by methods described previously to provide a compound of formula 53.

Again referring to Scheme XI, the dimethylaminomethylene bicyclic ketone of formula 51 in a suitable solvent such as ethanol may be treated with a suitable base, for instance potassium carbonate and an amidine or guanidine or salt thereof, one such example is illustrative, such as acetamidine hydrochloride. The reaction mixture at heated at under reflux until complete, typically for up to 7 days, preferably for 24–48 hours to provide a compound of formula 54. The benzyl group my be removed by standard methods, for instance treatment in ethanol with ammonium formate and a suitable protecting group precursor, such as di-t-butyl carbonate and a catalyst such as a palladium or platinum catalyst for instance Pearlman's catalyst. The mixture is heated at reflux until complete, for example, for 18 hours. This method works to convert the benzyl group into a compound of formula 55 whereby the nitrogen is protected as a t-butyl carbonyl group which is readily removed by methods well established in the art such as treatment of a solution of this material with HCl in alcohol, chlorinated solvent, ester or ethereal solvents, for convenience ethyl acetate or methanol is used usually at room temperature to provide a compound of formula 56.

Again referring to Scheme XI, the dimethylaminomethylene bicyclic ketone of formula 51 may be treated with hydrazine or substituted hydrazines to prepare pyrrazoles. For instance phenyl hydrazine hydrochloride in an alcoholic solvent when heated at reflux for 24–72 hours provides a pyrrazole of formula 57. This may be deprotected as described above to provide a compound of formula 58. Examples of these are described in the examples section.

Scheme XII

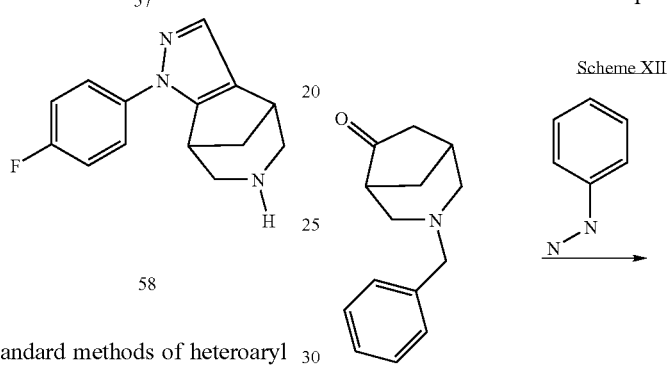

50

59

60

Referring to Scheme XII, ketone intermediates such as 50 and homologous ketones prepared by known methods or by methods related to those described herein (50a and 50b, Scheme X) may be converted to fused heteroaryl compounds of the invention of formulas V–VI under Fischer indole synthetic protocols. Under these conditions, such as by intimate contact, with or without solvent, preferably without, in the presence of a suitable catalyst, such as mineral acids, including sulfuric acid or organic acids such as tosic acid and the like, or Lewis acids such as zinc chloride, preferably zinc chloride or sulfuric acid, in amounts ranging from 0.1% to 200% of the weight of the mixture of components produces compound of formula 59. If the protecting group is suitably robust and survives the protocol, it requires subsequent removal by methods described previously. If however the protecting group is lost in the cyclization event, the compound may be isolated directly or by the intermediacy of protecting groups that facilitate purification by one skilled in the art and subsequent isolation of homogeneous materials of the invention. For brevity the formation of indole from phenyl hydrazine is shown, however other hydrazines are well know to participate in this reaction, such as 2, 3, or 4-substituted pyridinyl hydrazines and may be used to prepare additional heterocyclic compounds of formulas I, V and VI.

Scheme XIII

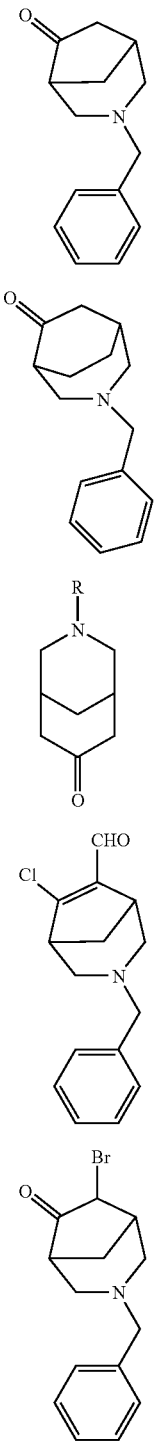

Referring to Scheme XIII, an additional method of generating fused heterocyclic compounds of the invention is by conversion of the ketone intermediates such 50 and homologous ketones such as 50a or 50b prepared by known methods such as those referred to above to reactive intermediates by treatment with conditions of Vilsmeier-Haack (Huet, F. *Synthesis* 1985, 5, 496–497 and Adam, W.; Richter, M. J. *J. Org. Chem.* 1994, 59, 3341–3346). These methods include but are not limited to treatment of a solution of ketone in a suitable reactive solvent such as dimethylformamide, with a suitable acid chloride such as phosphorous oxychloride or thionyl or oxalyl chloride. This is typically done at temperatures from 0–100° C., most preferably initiating the conversion at 0° C. and providing enough heat to promote conversion such as by allowing the mixture to warm to ambient temperature. Though chloride ligands are typically used, other halides may be used for this conversion. Subsequently the intermediate halo-aldehyde compounds (61 is depicted) produced in this way are useful in the generation of products of the invention by exposure to 2, 3, or 4-amino substituted pyridinyl compounds as desired. In such instances, the mixture of these two component compounds provides a method of condensation and thermal cyclization to generate compounds such as those described above in Scheme XI in the context of the Friedlander synthesis (see *Heterocycles* 1995, 41, 911–19 and *J. Org. Chem.* 1991, 56, 2268–70). Structure 61 and related structures are also suitable intermediates for the conversion to pyrimidines (with guanidines) and pyrimidones (with ureas) *J. Heterocyclic Chem.* 1995, 32, 353–4 and *Nippon Kagaku Kaishi* 1982, 5, 876–9).

Again referring to Scheme XIII, ketone intermediates such 50 and homologous ketones such as 50a or 50b may be converted to fused heteroaryl compounds of the invention after conversion to the corresponding alpha halo-ketone derivative such as 62. Treatment of such ketones or their alkali metal salts with halogenating agents such as with bromine provides access to 62 (for examples, see *J. Org. Chem.* 1986, 51, 2913–27). These intermediates are converted upon treatment with 2-amino heteroaryl compounds to fused heterocyclic compounds of the invention. This conversion may be carried out by known methods (see *Chem. Pharm. Bull.* 2000, 48, 935–940 and *J. Med. Chem.* 1999, 42, 3934–3941). Additionally the conversion of halo ketones of this type to imidazoles are known. (*Synthesis* 2000, 10, 1439–1443.)

As noted above, suitable amine protecting groups that can be used, alternatively, in the procedures described throughout this document include —$COCF_3$, —$COCCl_3$, —$COOCH_2CCl_3$, —$COO(C_1-C_6)$alkyl and —$COOCH_2C_6H_5$. These groups may be removed by methods described for each in Greene, et al., *Protective Groups in Organic Chemistry*, referred to above. Instances where protecting groups would be modified under the reaction conditions, such as, e.g., a —$COOCH_2C_6H_5$ group during nitration, still permit said procedures to operate as described with said modified protecting group. Modifying the order of protecting group incorporation and/or methods of functional group introduction or modification may also be applied where appropriate.

In each of the reactions discussed above, or illustrated in Schemes I–XI, above, pressure is not critical unless otherwise indicated. Pressures from about 0.5 atmospheres to about 5 atmospheres are generally acceptable, with ambient pressure, i.e., about 1 atmosphere, being preferred as a matter of convenience.

The compounds of the invention and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically and this can be done by way of creams, a patch, jellies, gels, pastes, ointments and the like, in accordance with standard pharmaceutical practice.

The effectiveness of the active compounds in suppressing nicotine binding to specific receptor sites is determined by the following procedure which is a modification of the methods of Lippiello, P. M. and Fernandes, K. G. (in *The Binding of L-[$^3$H]Nicotine To A Single Class of High-Affinity Sites in Rat Brain Membranes, Molecular Pharm.*, 29, 448–54, (1986)) and Anderson, D. J. and Americ, S. P. (in *Nicotinic Receptor Binding of $^3$H-Cystisine, $^3$H-Nicotine and $^3$H-Methylcarmbamylcholine In Rat Brain, European J. Pharm.*, 253, 261–67 (1994)).

The effectiveness of the active compounds in suppressing nicotine binding to specific receptor sites can be determined by the following procedure, which is a modification of the methods of Lippiello, P. M. and Fernandes, K. G. (in "The Binding of L-[$^3$H]Nicotine To A Single Class of High-Affinity Sites in Rat Brain Membranes", *Molecular Pharm.*, 29, 448–54, (1986)) and Anderson, D. J. and Arneric, S. P. (in "Nicotinic Receptor Binding of $^3$H-Cytisine, $^3$H-Nicotine and $^3$H-Methylcarmbamylcholine In Rat Brain", *European J. Pharm.*, 253, 261–67 (1994)). Male Sprague-Dawley rats (200–300 g) from Charles River were housed in groups in hanging stainless steel wire cages and were maintained on a 12-hour light/dark cycle (7 a.m.–7 p.m. light period). They received standard Purina Rat Chow and water ad libitum. The rats were killed by decapitation. Brains were removed immediately following decapitation. Membranes were prepared from brain tissue according to the methods of Lippiello and Fernandez (*Molec. Pharmacol.*, 29, 448–454, (1986)) with some modifications. Whole brains were removed, rinsed with ice-cold buffer, and homogenized at 0° C. in 10 volumes of buffer (w/v) using a Brinkmann Polytron™ (Brinkmann Instruments Inc., Westbury, N.Y.), setting 6, for 30 seconds. The buffer consisted of 50 mM Tris HCl at a pH of 7.5 at room temperature. The homogenate was sedimented by centrifugation (10 minutes; 50,000×g; 0 to 4° C.). The supernatant was poured off and the membranes were gently resuspended with the Polytron and centrifuged again (10 minutes; 50,000×g; 0 to 4° C.). After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM MgCl$_2$, 2 mM CaCl$_2$ and had a pH of 7.4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 µL of vehicle, blank, or test compound solution, respectively. To each tube was added 200 µL of [$^3$H]-nicotine in assay buffer followed by 750 µL of the membrane suspension. The final concentration of nicotine in each tube was 0.9 nM. The final concentration of cytisine in the blank was 1 µM. The vehicle consisted of deionized water containing 30 µL of 1 N acetic acid per 50 mL of water. The test compounds and cytisine were dissolved in vehicle. Assays were initiated by vortexing after addition of the membrane suspension to the tube. The samples were incubated at 0 to 4° C. in an iced shaking water bath. Incubations were terminated by rapid filtration under vacuum through Whatman GF/B™ glass fiber filters (Brandel Biomedical Research & Development Laboratories, Inc., Gaithersburg, Md.) using a Brandel™ multi-manifold tissue harvester (Brandel Biomedical Research & Development Laboratories, Inc., Gaithersburg, Md.). Following the initial filtration of the assay mixture, filters were washed two times with ice-cold assay buffer (5 ml each). The filters were then placed in counting vials and mixed vigorously with 20 ml of Ready Safe™ (Beckman, Fullerton, Calif.) before quantification of radioactivity. Samples were counted in a LKB Wallac Rackbeta™ liquid scintillation counter (Wallac Inc., Gaithersburg, Md.) at 40–50% efficiency. All determinations were in triplicate.

Calculations: Specific binding (C) to the membrane is the difference between total binding in the samples containing vehicle only and membrane (A) and non-specific binding in the samples containing the membrane and cytisine (B), i.e., Specific binding=(C)=(A)-(B).

Specific binding in the presence of the test compound (E) is the difference between the total binding in the presence of the test compound (D) and non-specific binding (B), i.e., (E)=(D)-(B).

% Inhibition=(1-((E)/(C)) times 100.

The compounds of the invention that were tested in the above assay exhibited $IC_{50}$ values of less than 100 µM.

[$^{125}$I]-Bungarotoxin Binding to Nicotinic Receptors in $GH_4Cl$ Cells:

Membrane preparations were made for nicotinic receptors expressed in $GH_4Cl$ cell line. Briefly, one gram of cells by wet weight were homogenized with a polytron in 25 mls of buffer containing 20 mM Hepes, 118 mM NaCl, 4.5 mM KCl, 2.5 mM $CaCl_2$, 1.2 mM $MgSO_4$, pH 7.5. The homogenate was centrifuged at 40,000×g for 10 min at 4° C., the resulting pellet was homogenized and centrifuged again as described above. The final pellet was resuspended in 20 mls of the same buffer. Radioligand binding was carried out with [$^{125}$I] alpha-bungarotoxin from New England Nuclear, specific activity about 16 uCi/ug, used at 0.4 nM final concentration in a 96 well microtiter plate. The plates were incubated at 37° C. for 2 hours with 25 µl drugs or vehicle for total binding, 100 µl [$^{125}$I] Bungarotoxin and 125 µl tissue preparation. Nonspecific binding was determined in the presence of methyllycaconitine at 1 µM final concentration. The reaction was terminated by filtration using 0.5% Polyethylene imine treated Whatman GF/B™ glass fiberfilters (Brandel Biomedical Research & Development Laboratories, Inc., Gaithersburg, Md.) on a Skatron cell harvester (Molecular Devices Corporation, Sunnyvale, Calif.) with ice-cold buffer, filters were dried overnight, and counted on a Beta plate counter using Betaplate Scint. (Wallac Inc., Gaithersburg, Md.). Data are expressed as IC50's (concentration that inhibits 50% of the specific binding) or as an apparent Ki, IC50/1+[L]/KD. [L]=ligand concentration, KD=affinity constant for [$^{125}$I] ligand determined in separate experiment.

The compounds of the invention that were tested in the above assay exhibited $IC_{50}$ values of less than 10 µM.

[$^{125}$I]-Bungarotoxin Binding to Alpha1 Nicotinic Receptors in Torpedo Electroplax Membranes:

Frozen Torpedo electroplax membranes (100 µl) were resuspended in 213 mls of buffer containing 20 mM Hepes, 118 mM NaCl, 4.5 mM KCl, 2.5 mM $CaCl_2$, 1.2 mM $MgSO_4$, pH 7.5 with 2 mg/ml BSA. Radioligand binding was carried out with [$^{125}$I] alpha-bungarotoxin from New England Nuclear, specific activity about 16 uCi/ug, used at 0.4 nM final concentration in a 96 well microtiter plate. The plates were incubated at 37° C. for 3 hours with 25 µl drugs or vehicle for total binding, 100 µl [$^{125}$I] Bungarotoxin and 125 µl tissue preparation. Nonspecific binding was determined in the presence of alpha-bungarotoxin at 1 µM final concentration. The reaction was terminated by filtration using 0.5% Polyethylene imine treated GF/B filters on a Brandel cell harvester with ice-cold buffer, filters were dried overnight, and counted on a Beta plate counter using Betaplate Scint.

Data are expressed as IC50's (concentration that inhibits 50% of the specific binding) or as an apparent Ki, IC50/1+[L]/KD. [L]=ligand concentration, KD=affinity constant for [$^{125}$I] ligand determined in separate experiment.

The following experimental examples illustrate, but do not limit the scope of, this invention.

Experimental Procedures

EXAMPLE 1

Preparation of 3-Cyclopent-3-enyl-(2-methoxy-pyridin-3-yl)-methanone (Based on Comins, D. L.; LaMunyon, D. H. *Tetrahedron Lett.* 1988, 29, 773–776 and Trecourt, F.; Mallet, M.; Marsais, F.; Queguiner, G. *J. Org. Chem.* 1988, 53, 1367–1371.)

Bromo-2,4,6-trimethylbenzene (16.9 g, 85 mmol) was stirred in anhydrous THF (340 mL) at −78° C. under nitrogen and treated with t-BuLi (100 mL of 1.7 M soln. in pentane, 170 mmol) dropwise via an addition funnel over 30 min. A yellow slurry forms and is stirred 1 h. To this was added 2-methoxypyridine (8.45 g, 77.3 mmol) in anhydrous THF (10 mL) over 5 min. The mixture was allowed to warm to 0° C. and stirred for 1 h, then at ambient temperature for 1 h, then recooled to −78° C. and treated with cyclopent-3-enecarboxylic acid methoxy-methyl-amide (12.4 g, 80 mmol) in anhydrous THF (20 mL) over 5 min. The resulting mixture was stirred 18 h (the bath evaporated and the mixture achieved ambient temperatures). The mixture was poured into saturated aqueous $NaHCO_3$ solution (250 mL) and stirred 20 min. The mixture was extracted with $Et_2O$ (3×100 mL). The organic layer was washed with $H_2O$ (2×100 mL) and saturated aqueous NaCl solution then dried over $Na_2SO_4$, filtered and concentrated to an oil (26 g). Purification by chromatography on silica gel eluting first with hexane to remove mesitylene followed by 10% then 20% $Et_2O$/hexanes elutes product, which was concentrated to a clear oil (12.2 g, 75% crude). (TLC 10% $Et_2O$/hexanes $R_f$ 0.36); $^1$H NMR (400 MHz, $CDCl_3$) δ 8.28 (dd, J=4.9, 2.0 Hz, 1H), 8.02 (m, 1H), 6.97 (m, 1H), 5.65 (s, 2H), 4.03 (s, 3H), 4.17, (m, 1H), 2.67 (m, 4H); GCMS m/z 203 (M)$^+$.

Preparation of
3-Cyclopent-3-enylmethyl-2-methoxy-pyridine

Cyclopent-3-enyl-(2-methoxy-pyridin-3-yl)-methanone (10.0 g, 49.3 mmol), hydrazine hydrate (6.33 g, 198 mmol) and pulverized potassium hydroxide (85% KOH) (16.8 g, 300 mmol) were warmed in ethylene glycol (100 mL) until solution occurred at 100° C. then to 180° C. for 18 h. The mixture was cooled to room temperature and treated with water (100 mL) then extracted with 50% EtOAc/hexanes (3×80 mL). The organic layer was washed with saturated aqueous NaCl solution, dried over $Na_2SO_4$ and concentrated to an oil. Purification by chromatography on silica gel eluting with 10% EtOAc/hexanes provided the desired product as an oil 4.75 g (51%). (TLC 10% $Et_2O$/hexanes $R_f$ 0.80); $^1$H NMR (400 MHz, $CDCl_3$) δ 8.01 (dd, J=5.0, 1.7 Hz, 1H), 7.37 (dd, J=7.2, 1.5 Hz, 1H), 6.81 (dd, J=7.2, 5.0 Hz, 1H), 5.66 (s, 2H), 3.95 (s, 3H), 2.61 (m, 3H), 2.40 (m, 2H), 2.03 (m, 2H); GCMS m/z 189 (M)⁺. 3-Cyclopent-3-enyl-1H-pyrazolo[3,4-b]pyridine was also isolated 4.45 g (49%).

Preparation of 3-Cyclopent-3-enylmethyl-1H-pyridin-2-one ester

3-Cyclopent-3-enylmethyl-2-methoxy-pyridine (2.1 g, 11.1 mmol) and NaI (4.16 g, 27.8 mmol) were stirred in dry $CH_3CN$ (25 mL). The resulting cloudy dispersion was stirred and treated with trimethylsilyl chloride (3.0 g, 27.8 mmol) causing the mixture to become a white dispersion. After stirring 30 min. at room temperature then at 70° C. for 1 h the reaction mixture was cooled to room temperature and treated with $H_2O$ (50 mL). The product precipitated, and was extracted with EtOAc (4×50 mL). The organic layer was washed with $H_2O$ (4×50 mL), saturated aqueous $NaHCO_3$ solution (50 mL) and saturated aqueous NaCl solution. The extracts were dried over $Na_2SO_4$ and concentrated to a yellow solid, 1.93 g (100%). (TLC 10% EtOAc $R_f$ 0.35); $^1H$ NMR (400 MHz, $CDCl_3$) δ 7.28 (m, 2H), 6.22 (t, J=6.6 Hz, 1H), 5.65 (s, 2H), 2.70 (m, 1H), 2.58 (d, J=7.5 Hz, 2H), 2.47 (m, 2H), 2.03 (m, 2H); $^{13}C$ NMR (100 MHz, $CDCl_3$) δ 165.1, 138.7, 132.3, 132.0, 129.6, 106.6, 38.7, 36.7, 35.2; GCMS m/z 175 (M)⁺.

Preparation of Trifluoro-methanesulfonic acid 3-cyclopent-3-enylmethyl-pyridin-2-yl ester 3-Cyclopent-3-enylmethyl-1H-pyridin-2-one (1.9 g, 10.9 mmol) and 2,6-dimethylpyridine (2.21 mL, 19 mmol) were stirred in dichloromethane (50 mL) at 0° C. and treated with trifluoromethanesulfonic anhydride (2.38 mL, 14.1 mmol) dropwise over 1 min. The mixture was allowed to warm to room temperature and stirred for 1 h then poured into $H_2O$ (50 mL). The layers were separated and the aqueous layer was extracted with dichloromethane (3×30 mL). The combined organic layer was washed with $H_2O$ (2×50 mL), and a saturated aqueous $NaHCO_3$ solution (50 mL), dried through a cotton plug and concentrated to provide an oil (3.1 g, 93%). (TLC 15% EtOAc/hexanes $R_f$ 0.40); $^1H$ NMR (400 MHz, $CDCl_3$) δ 8.21 (d, J=4.7 Hz, 1H), 7.70 (d, J=7.5 Hz, 1H), 7.29 (m, 1H), 5.67 (s, 2H), 2.74 (d, J=7.5 Hz, 2H), 2.61 (m, 1H), 2.45 (m, 2H), 2.04 (dd, J=14.3, 5.0 Hz, 2H); $^{13}C$ NMR (100 MHz, $CDCl_3$) δ 155.1, 145.8, 141.4, 129.5, 128.0, 124.0, 38.5, 36.9, 35.5, $CF_3$ carbon not observed; GCMS m/z 241 (M)⁺.

Preparation of 3-Aza-tricyclo[7.2.1.0$^{2,7}$]dodeca-2(7), 3,5,10-tetraene

Trifluoro-methanesulfonic acid 3-cyclopent-3-enylmethyl-pyridin-2-yl ester (3.1 g, 10.1 mmol) was stirred in DMF (20 mL) and degassed (3 $N_2$/vacuum cycles) then treated under a $N_2$ atmosphere with triethylamine (1.52 g, 15 mmol), 1,3-bis(diphenylphosphino)propane (334 mg, 0.80 mmol) and palladium acetate (72 mg, 0.32 mmol). After 20 min. the mixture was warmed to 100° C. under nitrogen for 18 h, at which time the reaction was deemed 90% complete. Additional triethylamine (1 mL, 7.2 mmol) was added and the mixture brought to 110° C. for 6 h at which time TLC analysis indicated complete consumption of starting material. The reaction mixture was cooled and poured into 50% saturated aqueous NaCl solution (75 mL) then extracted with EtOAc (4×30 mL). The combined organic layer was washed with $H_2O$ (2×50 mL), saturated aqueous $NaHCO_3$ solution (50 mL), saturated aqueous NaCl solution (50 mL), dried over $Na_2SO_4$, filtered and concentrated to an oil, 2.3 g. Of this material 1.89 g was chromatographed on silica gel eluting with 20% EtOAc/hexanes to provide an oil (1.07 g, 77%). (TLC 20% EtOAc/hexanes $R_f$ 0.21); $^1H$ NMR (400 MHz, $CDCl_3$) δ 8.10 (dd, J=4.9, 0.7 Hz, 1H), 7.18 (d, J=7.5 Hz, 1H), 6.92 (dd, J=7.5, 4.9 Hz, 1H), 6.21 (dd, J=5.5, 2.9 Hz, 1H), 5.73 (dd, J=5.5, 2.6 Hz, 1H), 3.43 (m, 1H), 2.86 (m, 2H), 2.40 (d, J=16.2 Hz, 1H), 2.21 (m, 1H), 1.80 (d, J=10.2 Hz, 1H); $^{13}C$ NMR (100 MHz, $CDCl_3$) δ 162.0, 145.0, 138.2, 138.0, 131.7, 130.1, 121.6, 47.3, 39.5, 37.9, 29.7; APCl MS m/z 158.1 (M)⁺.

Preparation of 3-Aza-tricyclo[7.2.1.0$^{2,7}$]dodeca-2(7),3,5-triene-10,11-diol 3-Aza-tricyclo[7.2.1.0$^{2,7}$]dodeca-2(7),3,5,10-tetraene (960 mg, 6.1 mmol) and trimethylamine N-oxide dihydrate (748 mg, 6.73 mmol) were stirred in dichloromethane (15 mL) and treated with osmium tetroxide ($OsO_4$, 0.2 mL of a 15 mol % t-butanol solution) and the mixture was stirred vigorously. After 18 h, the residue was poured onto a silica gel column (2×6 inch) and eluted with hexanes (100 mL) then EtOAc to elute product as an oil that crystallizes on standing (1.16 g, 100%). (TLC EtOAc $R_f$ 0.17); $^1H$ NMR (400 MHz, $CDCl_3$) δ 8.12 (d, J=4.9 Hz, 1H), 7.40 (d, J=7.5 Hz, 1H), 7.07 (dd, J=7.5, 4.9 Hz, 1H), 4.19 (d, J=6.0 Hz, 1H), 3.90 (d, J=6.0 Hz, 1H), 3.45 (s, 1H), 3.00 (dd, J=17.3, 4.8 Hz, 1H), 2.67 (d, J=17.3 Hz, 1H), 2.43 (m, 2H), 1.59 (d, J=11.6 Hz, 1H); $^{13}C$ NMR (100 MHz, $CDCl_3$) δ 159.4, 147.6, 138.1, 130.9, 122.3, 77.1, 75.4, 51.6, 42.2, 33.9, 28.5; APCl MS m/z 192.1 (M)⁺.

Preparation of 11-Benzyl-3,11-diaza-tricyclo[7.3.1.0$^{2,7}$]trideca-2(7),3,5-triene 3-Aza-tricyclo[7.2.1.0$^{2,7}$]dodeca-2(7),3,5-triene-10,11-diol (1.16 g, 6.07 mmol) was stirred in EtOH (40 mL) and was treated with a solution of $NaIO_4$ (1.35 g, 6.07 mmol) in $H_2O$ (20 mL). A precipitate forms and the mixture becomes a yellow slurry. After 15 min, the reaction is deemed complete (TLC EtOAc $R_f$ 0.62), diluted with water and extracted with dichloromethane (4×50 mL). The organic layer was washed with $H_2O$ (5×50 mL) then dried through a cotton plug and concentrated to an oil. This oil was stirred in DCE (50 mL), treated with benzyl amine (650 mg, 6.07 mmol) then sodium triacetoxyborohydride $NaBH(OAc)_3$ (4.12 g, 19.4 mmol). The mixture was stirred 7 h, then was quenched by addition to saturated sodium carbonate ($Na_2CO_3$) solution and EtOAc (~75 mL each). After stirring 20 min., the layers were separated and the aqueous layer was extracted with EtOAc (2×50 mL). The organic layer was washed with $H_2O$ (50 mL) and saturated aqueous NaCl solution (50 mL) then dried over $Na_2SO_4$. Filtration and concentration affords an oil, 1.2 g which was purified by chromatography on silica gel eluting with 50% EtOAc/hexanes to provide pure product as an oil, 802 mg (50%). (TLC EtOAc $R_f$ 0.68); $^1H$ NMR (400 MHz, $CDCl_3$) δ 8.30 (dd, J=4.7, 0.6 Hz, 1H), 7.40 (d, J=7.7 Hz, 1H), 7.13–7.07 (m, 4H), 6.85 (m, 2H), 3.35 (AB q, ΔAB=27.2, J=13.8 Hz, 2H), 3.08 (s, 1H), 3.02 (dd, J=17.3, 7.0 Hz, 1H), 2.92 (d, J=10.6 Hz, 1H), 2.81 (d, J=10.6 Hz, 1H), 2.74 (d, J=17.3 Hz, 1H) 3.34 (br d, J=10.6 Hz, 2H), 2.17 (br s, 1H), 1.90 (d, J=3.0 Hz, 2H); $^{13}C$ NMR (100 MHz, $CDCl_3$) δ 160.8, 145.6, 139.2, 134.7, 134.2, 128.1, 128.0, 126.6, 121.0, 62.3, 60.8, 58.9, 38.4, 34.2, 29.8, 28.4; APCl MS m/z 265.1 (M)⁺.

Preparation of 3,11-Diaza-tricyclo[7.3.1.0$^{2,7}$]trideca-2(7),3,5-triene

11-Benzyl-3,11-diaza-tricyclo[7.3.1.0$^{2,7}$]trideca-2(7),3,5-triene (743 mg, 2.8 mmol) and $HCO_2NH_4$ (6 g) were dissolved in methanol (35 mL) and treated with Pd(OH)$_2$/C (10 wt %, 210 mg). The mixture was warmed to reflux for 1 h then was filtered hot through Celite™ with a methanol rinse. The filtrate was stripped and slurried in dichloromethane then filtered through a fritted-glass filter. The filtrate was concentrated and dissolved in dichloromethane (15 mL) then treated with t-Boc$_2$O (670 mg, 3.1 mmol) and stirred 18 h. The mixture was stripped and purified by chromatography on silica gel eluting with 75% EtOAc/hexanes to provide pure product as an oil (224 mg, 30%). (TLC EtOAc R$_f$ 0.53). The remaining material was the N-formyl derivative, 3,11-diaza-tricyclo[7.3.1.0$^{2,7}$]trideca-2,4,6-triene-11-carbaldehyde, 360 mg (63%). GCMS m/z 202 (M)$^+$. 3,11-Diaza-tricyclo [7.3.1.0$^{2,7}$]trideca-2(7),3,5-triene-11-carbaldehyde and NaOH (800 mg) were warmed to reflux in dioxane/H$_2$O (7/3 mL) for 4 h. Additional NaOH was added (400 mg) and heating continued. After 2 h, the mixture was cooled, diluted with saturated aqueous NaHCO$_3$ solution (20 mL) and treated with t-Boc$_2$O (400 mg, 1.83 mmol) and stirred 2 h. Isolation as above yields 11-t-Boc-3,11-diaza-tricyclo[7.3.1.0$^{2,7}$] trideca-2(7),3,5-triene, 245 mg.

11-t-Boc-3,11-Diaza-tricyclo[7.3.1.0$^{2,7}$]trideca-2(7),3,5-triene (194 mg) was dissolved in EtOAc (5 mL) and treated with 3N HCl EtOAc (2 mL). The solution was warmed to reflux and stirred 18 h. After cooling, the solids were filtered and rinsed with hexane then dried under vacuum to give 95 mg white solids. Mp 295–301° C. (dec.); (TLC ~0.2% NH$_3$/ 10% CH$_3$OH/dichloromethane R$_f$ 0.25); $^1$H NMR (400 MHz, CD$_3$OD) δ 8.72 (d, J=5.5 Hz, 1H), 8.43 (d, J=8.1 Hz, 1H), 7.94 (dd, J=8.1, 5.5 Hz, 1H), 3.71 (s, 1H), 3.58 (dd, J=13.3, 2.4 Hz, 1H), 3.51–3.40 (m, 3H), 3.33 (m, 1H), 3.18 (d, J=19.1 Hz, 1H), 2.67 (br s, 1H), 2.33 (d, J=13.6 Hz, 1H), 2.11 (d, J=13.6 Hz, 1H); $^{13}$C NMR (100 MHz, CDCl$_3$) δ 149.5, 147.5, 140.3, 138.0, 125.7, 48.9, 46.2, 30.9, 30.4, 25.4, 24.4; GCMS m/z 174 (M)$^+$; Anal. Calcd. for C$_{11}$H$_{14}$N$_2$2HCl: C, 53.45; H, 6.52; N, 11.33. Found C, 53.06; H, 6.49; N, 11.16.

EXAMPLE 2

Preparation of 11-Methyl-3,11-diaza-tricyclo [7.3.1.0$^{2,7}$]trideca-2(7),3,5-triene dihydrochloride 3,11-Diaza-tricyclo[7.3.1.0$^{2,7}$]trideca-2,4,6-triene-11-carbaldehyde (75 mg, 0.4 mmol) was stirred in 1M BH$_3$.THF complex (3 mL) at reflux for 18 h at which time additional 1M BH$_3$.THF complex was introduced (3 mL). Heating was continued for 3 days at which time the mixture was cooled and treated with 1N HCl (5 mL) and conc. HCl (1 mL) and the resulting mixture refluxed for 24 h. The mixture was cooled, treated with solid NaOH to achieve pH 10 and extracted with EtOAc (4×10 mL). The organic layer was washed with saturated aqueous NaCl solution (30 mL), dried over Na$_2$SO$_4$, filtered and concentrated to give 48 mg. This material was dissolved in MeOH and treated with 1 mL 3N HCl/EtOAc solution, stirred and concentrated. After recrystallization from MeOH/Et$_2$O, product was filtered and dried to give white solids (49 mg 59%). Mp 260–266° C.; (TLC ~0.2% NH$_3$/5% CH$_3$OH/dichloromethane R$_f$ 0.33); $^1$H NMR (400 MHz, CD$_3$OD) δ 8.73 (d, J=5.0 Hz, 1H), 8.42 (d, J=8.1 Hz, 1H), 7.95 (m, 1H), 3.78–3.15 (m, 7H), 2.82 (s, 3H), 2.74 (br s, 1H), 2.28 (d, J=13.6 Hz, 1H), 2.09 (d, J=13.6 Hz, 1H); GCMS m/z 188 (M$^+$).

EXAMPLE 3

Preparation of 2-fluoro-3-iodopyridine

Prepared according to J. Org. Chem. 1993, 7832: A solution of lithium diisopropylamide was prepared by addition of n-BuLi (46.4 ml, 2.5 M in hexanes, 0.12 mol) to a solution of diisopropyl amine (15 ml, 0.12 mol) in of anhydrous THF (200 ml) at 0° C. After stirring for ten minutes the solution was cooled to −78° C. Using a syringe pump 2-fluoropyridine (10 ml, 0.12 mol) was added neat over 2 min. The reaction mixture was stirred for 4 h at this temperature. A white precipitate formed. A solution of iodine (29.5 gm, 0.12 mol) in of anhydrous THF (100 ml) was added over 40 min via syringe pump while the reaction was kept at −78° C. The reaction mixture changed from white to yellow and finally to orange in color during this addition. The reaction mixture is quenched at −78° C. by adding of water (5 ml) followed by carefully pouring the mixture into an 1:1 mixture of saturated aqueous sodium bicarbonate and saturated aqueous sodium thiosulfate. The product was extracted into ether and the organic layer was washed with brine and then dried over Na$_2$SO$_4$ and evaporated in vacuo. The residue 22.2 gm (86%), which solidified, was purified by chromatography on silica gel eluting with 9/1 hexane/ethyl acetate to afford of the desired 2-fluoro-3-iodopyridine contaminated with 2-fluoro-4-iodopyridine (21 gm). $^1$H NMR (CDCl$_3$, 400 MHz) δ 8.17 (m, 2H), 6.95 (m, 1H); APCl MS m/z 224 (M)$^+$.

Preparation of Cyclopent-3-enyl-(2-fluoro-4-iodo-pyridin-3-yl)-methanone

A solution of lithium diisopropylamide was prepared by addition of n-BuLi (1.79 ml, 2.5M in hexanes, 4.5 mmol) to a solution of diisopropyl amine (589 ul, 4.5 mmol) in of anhydrous THF 9 ml) at −78° C. After stirring for twenty minutes the solution was treated with 2-fluoro-3-iodopyridine (1 gm, 4.5 mmol) in anhydrous THF (1.8 ml) via syringe pump over 10 min. The mixture was stirred for one hour at −78° C. A brown precipitate was formed. To this mixture was added via syringe pump over fifteen minutes cyclopent-3-enecarboxylic acid methoxy-methyl-amide (695 mg, 4.5 mmol) in anhydrous THF (1.8 ml). The reaction mixture was stirred at −78° C. for 30 min. whereupon the suspension transformed to a solution followed by an additional 2.5 h at −78° C. The reaction mixture was quenched at −78° C. by adding water (5 ml) followed by carefully pouring the mixture into saturated aqueous sodium bicarbonate. The product was extracted into ethyl acetate and the organic layer was washed with brine and then dried over Na$_2$SO$_4$ and evaporated in vacuo. The residue, 950 mg, was purified by chromatography on silica gel eluting with 9/1 hexane/ether to afford of the desired product (676 mg, 48%). $^1$H NMR (CDCl$_3$, 400 MHz) δ 7.88 (d, 1H, J=5 Hz), 7.70 (d, 1H, J=5 Hz), 5.67 (s, 2H), 3.79 (m, 1H), 2.79 (m, 2H), 2.62 (m, 2H). $^{13}$C NMR (CDCl$_3$, 100 MHz) δ 202.1, 159.2, 157.0, 148.1, 147.9, 132.7, 128.7, 106.6, 49.5, 34.9; APCl MS m/z 318 (M+1)$^+$. 2-Fluoro-3,4-diodopyridine was also isolated (60 mg). $^1$H NMR (CDCl$_3$, 400 MHz) δ 7.84 (d, 1H, J=5 Hz), 7.64 (d, 1H, J=5 Hz); $^{13}$C NMR (CDCl$_3$, 100 MHz) δ 163.9, 161.0, 147.0, 146.9, 132.2, 123.5, 92.0; APCl MS m/z 350 (M+1)$^+$.

Preparation of 6-Fluoro-5-aza-tricyclo[7.2.1.0$^{2,7}$] dodeca-2,4,6,10-tetraen-8-one Cyclopent-3-enyl-(2-fluoro-4-iodo-pyridin-3-yl)-methanone (110 mg, 0.35 mmol) as prepared above, was combined with tetrabutylammonium bromide (112 mg, 0.35 mmol), potassium acetate (102 mg, 1.04 mmol), triphenylphosphine (2 mg, 0.009 mmol) and DMF (4 ml). The reaction mixture was deoxygenated with nitrogen and then palladium acetate (2 mg, 0.008 mmol) was introduced. The reaction mixture was heated in a 100° C. oil bath for 20 min. A black precipitate was observed after 7 min. The reaction mixture was cooled to room temperature and was then added to a mixture of 1:1:1:1 ethyl acetate, hexane, brine and water. The organic layer was separated and washed with brine and then dried and evaporated. The residue (60 mg) was used directly in the next step. $^1$H NMR (CDCl$_3$, 400 MHz) δ 8.15 (d, 1H, J=5 Hz), 7.03 (d, 1H, J=5 Hz), 6.65 (m, 1H), 6.19 (m, 1H), 3.69 (br s, 1H), 3.51 (m, 1H), 2.68 (m, 1H), 2.63 (d, 1H, J=11 Hz); APCl MS m/z 190 (M+1)$^+$; HRMS (m/z): (M+H)$^+$ calc'd. for C$_{11}$H$_8$FNO$_2$: 190.0668; found, 190.0654.

Preparation of 6-Methoxy-5-aza-tricyclo[7.2.1.0$^{2,7}$]dodeca-2,4,6,10-tetraen-8-one The crude product from above (60 mg, 0.32 mmol) was taken up into methanol and treated with sodium methoxide (21 mg, 0.38 mmol) and heated under reflux for 30 min. The reaction mixture was allowed to cool to room temperature and was partitioned between dichloromethane and brine. The organic layer was dried over sodium sulfate and evaporated in vacuo. The residue was purified by chromatography on silica gel eluting with 85/15 hexanes/ethyl acetate to afford desired material 42 mg (60% overall). $^1$H NMR (CDCl$_3$, 400 MHz) δ 8.10 (d, 1H, J=5 Hz), 6.70 (d, 1H, J=5 Hz), 6.57 (dd, 1H, J=6 Hz, J=3 Hz), 6.17 (dd, 1H, J=6 Hz, J=3 Hz), 3.97 (s, 3H), 3.56 (br s, 1H), 3.43 (br s, 1H), 2.57 (m, 2H). $^{13}$C NMR (CDCl$_3$, 100 MHz) δ 193.9, 163.5, 159.8, 150.6, 142.1, 132.7, 114.1, 110.4, 57.5, 54.1, 47.2, 46.7; APCl MS m/z 202 (M+1)$^+$; HRMS (m/z): (M+H)$^+$ calc'd. for C$_{12}$H$_{11}$NO$_2$: 202.0868; found, 202.0880.

Preparation of 6-Methoxy-5-aza-tricyclo[7.2.1.0$^{2,7}$]dodeca-2,4,6,10-tetraene A flame dried round bottom flask with nitrogen inlet, magnetic stir bar and a reflux condenser was charged with 6-methoxy-5-aza-tricyclo[7.2.1.0$^{2,7}$]dodeca-2,4,6,10-tetraen-8-one (0.58 gm, 2.9 mmol) and tosylhydrazine (0.59 gm, 3.2 mmol) in 100% ethanol (5 ml). The reaction was heated under reflux for 30 min. The mixture was allowed to cool to room temperature and was then filtered. The solids were washed with ethanol and then dried under vacuum to afford the tosylhydrazone (0.8 gm, 80%). A second flame dried round bottom flask with nitrogen inlet and magnetic stir bar was charged with chloroform (6 ml, made EtOH free by passing through a column of alumina) followed by benzoic acid (1.1 gm, 8.65 mmol) and the mixture was cooled to 0° C. The reaction mixture was carefully treated with 1M BH$_3$.THF (4.3 ml, 4.3 mmol) causing vigorous evolution of hydrogen gas. Once addition was complete, the reaction mixture was stirred at 0° C. for one hour and was then treated with the tosylhydrazone (0.8 gm) prepared above and stirred for and additional hour at 0° C. To this mixture was charged with tetrabutylammonium bromide (0.5 gm) and then it was warmed to room temperature. The reaction mixture was evaporated in vacuo and then resuspended in ethylene glycol (5 ml) and treated with potassium carbonate (0.4 gm, 2.88 mmol). The reaction mixture was heated to 110° C. for one hour and then cooled to room temperature. The mixture was diluted with water (50 ml) and extracted with dichloromethane. The organic phase was washed with brine, dried over Na$_2$SO$_4$ and evaporated in vacuo to afford 330 mg of a residue that was purified by chromatography on silica gel eluting with dichloromethane to afford a clear oil (260 mg 48%). $^1$H NMR (CDCl$_3$, 400 MHz) δ 7.84 (d, 1H, J=5 Hz), 6.56 (d, 1H, J=5 Hz), 6.15 (dd, 1H, J=6 Hz, J=3 Hz), 5.82 (dd, 1H, J=6 Hz, J=3 Hz), 3.89 (s, 3H), 3.23 (t, 1H, J=4 Hz), 2.99 (br.s, 1H), 2.67 (dd, 1H, J=18 Hz, J=5 Hz), 2.34 (d, 1H, J=18 Hz), 2.17 (dt, 1H, J=10 Hz, J=5 Hz), 1.78 (d, 1H, J=10 Hz); APCl MS m/z 188 (M+1)$^+$.

Preparation of 6-Methoxy-5-aza-tricyclo[7.2.1.0$^{2,7}$]dodeca-2(7),3,5-triene-10,11-diol To a flame dried round bottomed flask equipped with a magnetic stir bar and nitrogen inlet was added 6-methoxy-5-aza-tricyclo[7.2.1.0$^{2,7}$]dodeca-2,4,6,10-tetraene (230 mg, 1.23 mmol) as prepared above) in 10 ml of anhydrous dichloromethane. The solution was treated with trimethylamine N-oxide (150 mg, 1.35 mmol) followed OsO$_4$ (10 drops, 2.5% in t-butanol. The reaction mixture was stirred at room temperature for 36 h and then added directly to a silica gel column and eluted with 98/2 dichloromethane/methanol. The desired diol was obtained and used in the following step (0.26 gm, 96%). $^1$H NMR (CDCl$_3$, 400 MHz) δ 7.85 (d, 1H, J=6 Hz), 6.60 (d, 1H, J=6 Hz), 4.02 (m, 2H), 3.90 (s, 3H), 3.28 (d, 1H, J=4 Hz), 3.00 (m, 2H), 2.75 (dd, 1H, J=18 Hz, J=5 Hz), 2.53 (d, 1H, J=18 Hz), 2.45 (m, 1H), 2.24 (dt, 1H, J=12 Hz, J=5 Hz), 1.52 (d, 1H, J=12 Hz); $^{13}$C NMR (CDCl$_3$, 100 MHz) δ 143.8, 117.0, 116.5, 112.0, 77.9, 77.6, 53.4, 48.5, 42.2, 30.4, 28.4 ppm; APCl MS m/z 222 (M+1)$^+$.

Preparation of 6-Methoxy-5,11-diaza-tricyclo[7.3.1.0$^{2,7}$]trideca-2(7),3,5-triene To a 250 ml Parr bottle was added 6-methoxy-5-aza-tricyclo[7.2.1.0$^{2,7}$]dodeca-2(7),3,5-triene-10,11-diol 250 mg (1.13 mmol) in of ethanol-water 3:1 (12 ml). The solution was treated with sodium periodate (240 mg, 1.13 mmol) in water (1 ml) and the mixture was stirred at room temperature for 2 h. A white precipitate was evident. The stir bar was removed and the reaction mixture is treated with of saturated aqueous ammonium hydroxide solution (10 ml), and Pearlman's catalyst (50 mg) placed under 45 psi hydrogen pressure for 16 h. The reaction mixture was vented and then filtered through Celite™. The filtrate was evaporated in vacuo. The residue was taken up in dichloromethane and washed with brine, dried over Na$_2$SO$_4$ and evaporated in vacuo. The residue was purified by chromatography on silica gel eluting with 95/5 dichloromethane/methanol to afford the desired product as an oil (125 mg, 54%). $^1$H NMR (CDCl$_3$, 400 MHz) δ 7.88 (d, 1H, J=5 Hz), 6.55 (d, 1H, J=5 Hz), 3.94 (s, 3H), 3.0 (dd, 1H, J=14 Hz, J=3 Hz), 2.96 (br.s, 2H), 2.80 (d, 1H, J=7 Hz), 2.76 (br.s, 2H), 2.56 (d, 1H, J=19 Hz), 2.07 (br.s, 1H), 1.95 (d, 1H, J=12 Hz), 1.82 (d, 1H, J=12 Hz). $^{13}$C NMR (CDCl$_3$, 100 MHz) δ 161.0, 150.0, 143.0, 121.2, 116.7, 53.9, 53.2, 51.9, 34.9, 29.2, 28.7, 27.3; APCl MS m/z 205 (M+1)$^+$.

EXAMPLE 4

Preparation of 11-Allyl-6-methoxy-11-aza-tricyclo[7.3.1.0$^{2,7}$]trideca-2(7),3,5-trien-8-one 6,7-Dihydroxy-1-methoxy-5,6,7,8-tetrahydro-5,8-methano-benzocyclohepten-9-one (2.80 g, 12 mmol) was stirred at 0° C. in dichloromethane (15 mL) and treated with lead tetraacetate (Pb(OAc)$_4$, 5.35 g, 12 mmol). After 30 min. the mixture was filtered through a Celite™ pad and rinsed with dichloromethane (50 mL). To the stirred filtrate was added AcOH (3.61 g, 60 mmol) and allyl amine (689 mg, 12 mmol). After 15 min., the mixture was treated with NaBH (OAc)₃ (7.70 g, 36 mmol) and stirred for 18 h. The mixture was poured into a saturated aqueous Na₂CO₃ solution (100 mL) stirred for 30 min. The layers were separated and extracted with EtOAc (2×100 mL). The organic layer was washed with a saturated aqueous Na₂CO₃ solution (2×50 mL), H₂O (50 mL), saturated aqueous NaCl solution (50 mL), dried over MgSO₄, filtered and concentrated to an oil. Purification by chromatography on silica gel eluting with 5% EtOAc/hexanes provided product as an oil (885 mg, 29%). (TLC 30% EtOAc/hexanes $R_f$ 0.67).

Preparation of 11-Allyl-6-hydroxy-11-aza-tricyclo[7.3.1.0²,⁷]trideca-2(7),3,5-trien-8-one 11-Allyl-6-methoxy-11-aza-tricyclo[7.3.1.0²,⁷]trideca-2(7),3,5-trien-8-one (1.20 g, 4.66 mmol) in dichloromethane (25 mL) was cooled to −78° C. and treated with BCl₃ (10.3 mL, 1M in dichloromethane). The mixture was allowed to stir to ambient temperature for 18 h. The mixture was treated with half saturated aqueous NaHCO₃ solution (100 mL), the layers were separated and extracted with dichloromethane (3×40 mL). The organic layer was washed with H₂O (50 mL) and saturated aqueous NaCl solution (50 mL), dried through a cotton plug and concentrated to an oil. Purification by chromatography on silica gel eluting with 15% EtOAc/hexanes afforded an oil (500 mg, 44%). (TLC 25% EtOAc/hexanes $R_f$ 0.52); ¹H NMR (400 MHz, CDCl₃) δ 7.33 (dd, J=8.3, 7.5 Hz, 1H), 6.78 (dd, J=8.3, 1.0 Hz, 1H), 6.67 (dd, J=7.5, 1.0 Hz, 1H), 5.52 (m, 1H), 4.95 (m, 2H), 3.16 (br d, J=10.8 Hz, 1H), 3.05 (br s, 1H), 2.85 br, d, J=6.0 Hz, 2H), 2.78 (dd, J=9.5, 1.3 Hz, 1H), 2.65 (d, J=1.7 Hz, 1H), 2.41 (dd, J=10.8, 2.4 Hz, 1H), 2.33 (m, 2H), 1.86 (ddd, J=12.9, 5.9, 2.9 Hz, 1H); GCMS m/z 243 (M)⁺.

Preparation of Trifluoro-methanesulfonic acid 11-allyl-8-oxo-11-aza-tricyclo[7.3.1.0²,⁷]trideca-2(7),3,5-trien-6-yl ester 11-Allyl-6-hydroxy-11-aza-tricyclo[7.3.1.0²,⁷]trideca-2(7),3,5-trien-8-one (0.5 g, 2.05 mmol) and pyridine (326 mg, 4.11 mmol) were stirred in dichloromethane (25 mL) at −78° C. under N₂ and treated with trifluoromethane sulfonic anhydride (870 mg, 3.08 mmol) dropwise over 1 min. The mixture was allowed to warm to ambient temperature and stirred for 1/2 h then poured into 1N aqueous HCl solution and shaken. The layers were separated and the aqueous layer was extracted with dichloromethane (2×30 mL). The combined organic layer was washed with H₂O (50 mL), saturated aqueous NaHCO₃ solution (50 mL), dried through a cotton plug, concentrated and purified by chromatography on silica gel eluting with 30% EtOAc/hexanes to provide an oil (605 mg, 79%). (TLC 30% EtOAc/hexanes $R_f$ 0.28).

Preparation of 11-Allyl-8-oxo-11-aza-tricyclo[7.3.1.0²,⁷]trideca-2(7),3,5-triene-6-carboxylic acid methyl ester Trifluoro-methanesulfonic acid 11-allyl-8-oxo-11-aza-tricyclo[7.3.1.0²,⁷]trideca-2(7),3,5-trien-6-yl ester (600 mg, 1.60 mmol) was dissolved in methanol (4 mL) and DMSO (10 mL) under a N₂ atmosphere and treated with triethylamine (356 g, 3.5 mmol), potassium acetate (16 mg, 0.16 mmol) and 1,3-bis(diphenylphosphine)propane (66 mg, 0.16 mmol). This mixture was stirred and degassed (3 vacuum/N₂ purge cycles) and then treated with palladium acetate (36 mg, 0.16 mmol). The reaction vessel was flushed with carbon monoxide for 1 minute (bubbling through a needle) then placed under the balloon. After 10 min. the mixture was warmed to 70° C. for 2 h, cooled and poured into saturated aqueous NaCl solution (50 mL). The resulting mixture was extracted with EtOAc (4×25 mL) and the combined organic layer was washed with H₂O (10 mL), saturated aqueous NaHCO₃ solution (10 mL) and saturated aqueous NaCl solution (10 mL), dried over MgSO₄, filtered, concentrated and purified by chromatography on silica gel eluting with 50% EtOAc/hexanes to provide an oil (260 mg, 57%). (TLC 50% EtOAc/hexanes $R_f$ 0.30); ¹H NMR (400 MHz, CDCl₃) δ 7.46 (d, J=7.5 Hz, 1H), 7.28 (d, J=7.5 Hz, 1H), 7.23 (dd, J=7.5, 1.3 Hz, 1H), 5.47 (m, 1H), 4.93 (m, 2H), 3.91 (s, 3H), 3.16 (dd, J=8.9, 1.6 Hz, 1H), 3.11 (d, J=1.9 Hz, 1H), 2.80 (m, 3H), 2.65 (d, J=1.7 Hz, 1H), 2.45 (dd, J=11.0, 2.5 Hz, 1H), 2.31 (m, 2H), 1.88 (ddd, J=12.8, 5.5, 2.7 Hz, 1H); GCMS m/z 285 (M)⁺; IR (cm⁻¹) 2941, 2786, 1732, 1685, 1286, 1146, 1142.

Preparation of

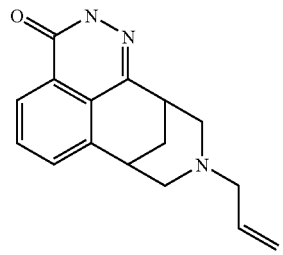

11-Allyl-8-oxo-11-aza-tricyclo[7.3.1.0²,⁷]trideca-2(7),3,5-triene-6-carboxylic acid methyl ester (60 mg, 0.21 mmol) and hydrazine were dissolved in ethanol (10 mL) and stirred for 18 h. The reaction was concentrated and azeotroped from methanol (3×25 mL). (TLC 35% EtOAc/hexanes $R_f$ 0.23); ¹H NMR (400 MHz, CDCl₃) δ 8.21 (dd, J=7.9, 1.1 Hz, 1H), 7.63 (t, J=7.9 Hz, 1H), 7.54 (d, J=7.9 Hz, 1H), 3.18 (br s, 1H), 3.09 (br s, 1H), 3.01 (d, J=10.9 Hz, 1H), 2.78 (m, 1H), 2.42 (m, 2H), 2.14–1.97 (m, 4H), 1.11 (m, 2H), 0.40 (t, J=7.5 Hz, 3H); ¹³C NMR (CDCl₃, 100 MHz, free base) δ 161.3, 149.8, 142.2, 139.0, 138.7, 129.4, 126.3, 124.1, 59.3, 59.0, 58.6, 36.2, 35.8, 31.9, 19.5, 11.2; APCI MS m/z 270.2 (M+1)⁺. This material was converted to the HCl salt by dissolving in MeOH and treating with 3N HCl EtOAc, stripping and recrystallizing from MeOH/Et₂O to provide a crystalline solid (60 mg, 93%). Mp 290–292° C.

EXAMPLE 5a

Preparation of

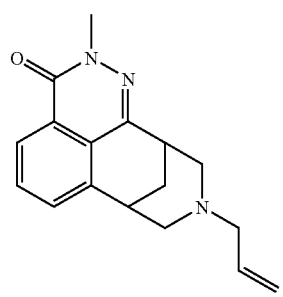

11-Allyl-8-oxo-11-aza-tricyclo[7.3.1.0$^{2,7}$]trideca-2(7),3,5-triene-6-carboxylic acid methyl ester (60 mg, 0.21 mmol) and methyl hydrazine were dissolved in ethanol (10 mL) and warmed to 70° C. for 1 h. The reaction was concentrated and azeotroped from methanol (3×25 mL) then filtered through a silica gel plug eluting with 50% EtOAc/dichloromethane to provide an oil (45 mg, 76%). (TLC 40% EtOAc/hexanes R$_f$ 0.27); $^1$H NMR (400 MHz, CDCl$_3$) δ 8.22 (dd, J=7.9, 1.2 Hz, 1H), 7.62 (dd, J=7.9, 7.3 Hz, 1H), 7.49 (d, J=7.3 Hz, 1H), 5.39 (m, 1H), 4.90–4.79 (m, 2H), 3.81 (s, 3H), 3.18 (br s, 1H), 3.06 (br s, 1H), 3.00 (br d, J=10.5 Hz, 1H), 2.80 (m, 3H), 2.43 (m, 2H), 2.04 (m, 2H).

EXAMPLE 5b

Preparation of

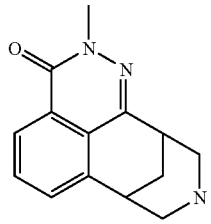

4,5-(1-Allyl-piperidin-3,5-yl)-2-methyl-2H-phthalazin-1-one (45 mg, 0.16 mmol) was dissolved in EtOH/H$_2$O (95/5, 10 mL) in a flask equipped with an equalizing addition funnel, a glass stopper and a distillation head. EtOH/H$_2$O (95/5, 20 mL) was introduced into the addition funnel and the solutions were degassed (4 evacuation/N$_2$ purge cycles). RhCl(PPh$_3$)$_3$ (6 mg, 0.0064 mmol) was added to the reaction vessel and the mixture was warmed to achieve a gentle distillation. EtOH/H$_2$O was added from the addition funnel to replace the distilled volume. After 15 mL had collected, additional RhCl(PPh$_3$)$_3$ (20 mg, 0.022 mmol) was added and distillation continued. After complete consumption of starting material, the solvent was evaporated and the product was purified by chromatography on silica gel eluting with 35% EtOAc/hexanes to provide a solid. Mp 320–322° C.; (TLC 35% EtOAc/hexanes R$_f$ 0.23); $^1$H NMR (400 MHz, CD$_3$OD) δ 8.29 (dd, J=7.9, 1.2 Hz, 1H), 7.70 (dd, J=7.9, 7.3 Hz, 1H), 7.54 (dd, J=7.3, 1.1 Hz, 1H), 3.83 (s, 3H), 3.21 (dd, J=12.5, 2.7 Hz, 1H), 3.15 (m, 3H), 2.98 (s, 1H), 2.89 (d, J=12.2 Hz, 1H), 2.25 (m, 3H); APCI MS m/z 242.2 (M+1)$^+$.

EXAMPLE 6

Preparation of 11-Allyl-6-hydroxymethyl-11-aza-tricyclo[7.3.1.02,7]trideca-2,4,6-trien-8-ol 11-Allyl-8-oxo-11-aza-tricyclo[7.3.1.0$^{2,7}$]trideca-2(7),3,5-triene-6-carboxylic acid methyl ester (109 mg, 0.40 mmol) was stirred in ethanol (10 mL) and treated with NaBH$_4$ (15 mg, 0.40 mmol). After 18 h, the reaction mixture was concentrated and treated with 1N HCl (50 mL) with stirring. After 30 min., the aqueous layer was extracted with Et$_2$O (3×50 mL), basified with saturated aqueous Na$_2$CO$_3$ solution and extracted with EtOAc (3×50 mL). The organic layer was washed with saturated aqueous NaHCO$_3$ solution (2×50 mL) and saturated aqueous NaCl solution, dried over MgSO$_4$, filtered and concentrated to give an oil (90 mg, 90%). (TLC 35% EtOAc/hexanes R$_f$ 0.23); $^1$H NMR (400 MHz, CDCl$_3$) δ 7.27 (dd, J=7.5, 1.5 Hz, 1H), 7.18 (t, J=7.5 Hz, 1H), 7.01 (dd, J=7.5, 1.5 Hz, 1H), 5.62 (m, 1H), 5.27 (t, J=4.0 Hz, 1H), 5.05 (m, 1H), 4.88 (d, J=12.1 Hz, 1H), 4.41 (d, J=12.1 Hz, 1H), 4.27 (OH), 3.72 (OH), 3.31 (ddd, J=12.4, 2.5, 1.7 Hz, 1H), 2.85 (m, 3H), 2.52 (m, 1H), 2.38 (m, 1H), 2.05 (dd, J=11.4, 1.7 Hz, 1H), 1.80 (m, 2H); $^{13}$C NMR (100 MHz, CDCl$_3$) δ 143.2, 140.3, 139.1, 134.9, 128.9, 127.7, 127.2, 118.5, 68.7, 64.0, 61.5, 59.9, 55.1, 36.3, 33.3, 32.1; IR (cm$^{-1}$) 3376, 3071, 2920, 2788, 1642, 1468, 1051, 796; APCI MS m/z 260.2 (M+1)$^+$.

Preparation of 11-Allyl-8-oxo-11-aza-tricyclo[7.3.1.02,7]trideca-2,4,6-triene-6-carbaldehyde 11-Allyl-6-hydroxymethyl-11-aza-tricyclo[7.3.1.0$^{2,7}$]trideca-2,4,6-trien-8-ol (93 mg, 0.36 mmol) was dissolved dichloromethane (8 mL) and treated with N-methylmorpholine N-oxide monohydrate (73 mg, 0.54 mmol), powdered 4 Å molecular sieves (180 mg) and TPAP (TETRAPROPYLAMMONIUM PERRUTHENATE) 6.0 mg, 0.02 mmol). After 18 h, the mixture was stripped, dissolved in EtOAc and filtered through a silica gel pad. The organic layer was washed with H$_2$O (2×30 mL), saturated aqueous NaCl solution (30 mL), dried over MgSO$_4$, filtered and concentrated to give an oil (75 mg, 81%). (TLC 30% EtOAc/hexanes R$_f$ 0.70); $^1$H NMR (400 MHz, CDCl$_3$) δ 10.62 (s, 1H), 7.62 (dd, J=7.9, 1.4 Hz, 1H), 7.54 (dd, J=7.9, 7.3 Hz, 1H), 7.43 (d, J=7.3 Hz, 1H), 5.46 (m, 1H), 4.93 (m, 2H), 3.19 (m, 2H), 2.82 (m, 3H), 2.73 (br s, 1H), 2.48 (dd, J=10.9, 2.4 Hz, 1H), 2.35 (m, 2H), 1.96 (ddd, J=12.8, 5.4, 2.7 Hz, 1H); $^{13}$C NMR (CDCl$_3$, 100 MHz, free base) δ 202.1, 194.5, 148.3, 138.0, 134.6, 134.0, 132.9, 131.6, 126.2, 117.3, 60.8, 57.8, 57.2, 44.1, 36.6, 32.0.

Preparation of

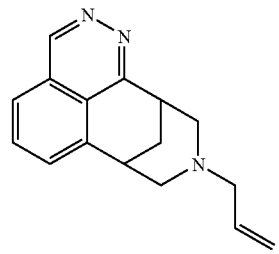

11-Allyl-8-oxo-11-aza-tricyclo[7.3.1.0$^{2,7}$]trideca-2,4,6-triene-6-carbaldehyde (75 mg, 0.29 mmol) was stirred in EtOH (5 mL) and treated with hydrazine (9.0 mg, 0.29 mmol). After 18 h, the reaction mixture was concentrated, treated with H$_2$O (50 mL) and extracted with dichloromethane (3×100 mL). The organic layer was dried through a cotton plug and concentrated to an oil (40 mg, 55%). (TLC 30% EtOAc/hexanes R$_f$ 0.14); $^1$H NMR (400 MHz, CDCl$_3$) δ 9.37(s, 1H), 7.73 (m, 2H), 7.58 (dd, J=6.5, 1.2 Hz, 1H), 5.28 (m, 1H), 4.81 (dd, J=10.1, 1.2 Hz, 1H), 4.72 (dddd, J=17.2, 5.0, 3.2, 1.5 Hz, 1H), 3.54 (br s, 1H), 3.29 (br s, 1H), 3.13 (br d, J=10.8 Hz, 1H), 2.84 (br d, J=10.8 Hz, 1H), 2.75 (m, 2H), 2.55 (dd, J=10.8, 2.3 Hz, 1H), 2.49 (dd, J 10.8, 2.2 Hz, 1H), 2.16 (AB m, 2H); APCI MS m/z 252.2 (M+1)$^+$. A sample was dissolved in MeOH and treated with 3N HCl EtOAc, concentrated to give the HCl salt, mp 233–234° C.

EXAMPLE 7

Preparation of 11-Allyl-6-hydroxy-11-aza-tricyclo [7.3.1.0$^{2,7}$]trideca-2(7), 3,5-trien-8-ol 11-Allyl-6-hydroxy-11-aza-tricyclo[7.3.1.0$^{2,7}$]trideca-2 (7),3,5-trien-8-one (420 mg, 1.72 mmol) was stirred in EtOH (10 mL) and treated with NaBH$_4$ (65 mg, 1.73 mmol). After 18 h, the reaction mixture was concentrated and treated with 1N HCl (50 mL) with stirring. After 30 min., the aqueous layer was extracted with Et$_2$O (3×50 mL), basified with saturated aqueous Na$_2$CO$_3$ solution and extracted with EtOAc (3×50 mL). The organic layer was washed with saturated aqueous NaHCO$_3$ solution (2×50 mL) and saturated aqueous NaCl solution, dried over MgSO$_4$, filtered and concentrated to give of an oil (350 mg, 1.42 mmol, TLC 30% EtOAc/ hexanes R$_f$ 0.34).

Preparation of

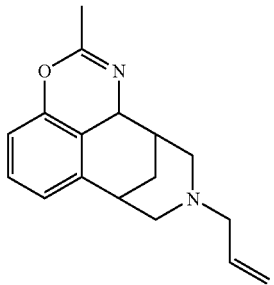

11-Allyl-6-hydroxy-11-aza-tricyclo[7.3.1.0$^{2,7}$]trideca-2 (7),3,5-trien-8-ol (350 mg, 1.42 mmol) was dissolved in CH$_3$CN (10 mL) and treated with H$_2$SO$_4$ (0.3 mL), stirred for 18 h, stripped of solvent then shaken in saturated aqueous Na$_2$CO$_3$ solution (50 mL). This aqueous layer was extracted with EtOAc (3×40 mL) and the organic layer was washed with saturated aqueous NaCl solution (30 mL), dried over MgSO$_4$, filtered and concentrated to an oil. This material was purified on silica gel eluting with 50% dichloromethane/hexanes to provide 200 mg of a solid that was recrystallized from ether/hexanes to give crystaline solid (150 mg, 40%). Mp 208–209° C.; (TLC 30% EtOAc/hexanes R$_f$ 0.50); $^1$H NMR (400 MHz, CDCl$_3$) δ 6.99 (dd, J=8.1, 7.5 Hz, 1H), 6.62 (dd, J=8.1, 1.0 Hz, 1H), 6.56 (d, J=7.5 Hz, 1H), 5.58 (m, 1H), 4.90 (m, 2H), 3.28 (br s, 1H), 3.10 (d, J=10.8 Hz, 1H), 2.84 (br s, 1H), 2.80 (m, 2H), 2.73 (br d, J=10.8 Hz, 1H), 2.22 (m, 2H), 2.05 (m, 1H), 1.88 (s, 3H), 1.65 (d, J=12.3 Hz, 1H).

EXAMPLE 8

Preparation of 11-Ally-6-hydroxy-11-aza-tricyclo [7.3.1.0$^{2,7}$]trideca-2,4,6-trien-8-one oxime 11-Allyl-6-methoxy-11-aza-tricyclo[7.3.1.0$^{2,7}$]trideca-2 (7),3,5-trien-8-one (243 mg, 1.0 mmol), hydroxylamine hydrochloride (80 mg, 1.15 mmol) an barium carbonate (227 mg, 1.15 mmol) were stirred and warmed to reflux in methanol (10 mL) for 18 h. Additional hydroxylamine hydrochloride (30 mg, 0.43 mmol) an barium carbonate (70 mg, 0.35 mmol) were introduced and heating continued for 2 h. The mixture was cooled to ambient temperature and filtered through Celite™, rinsed with methanol, concentrated and the residue dissolved in dichloromethane (30 mL), H$_2$O (30 mL) and saturated aqueous NaHCO$_3$ solution (~30 mL) to achieve pH 8.5. The layers were separated and the aqueous layer was extracted with dichloromethane (2×30 mL), dried through a cotton plug and concentrated to an oily solid (275 mg). This material was triturated with stirring for in dichloromethane (20 mL) for 60 h and the resulting orange solid filtered (100 mg, 39%). (TLC 20% EtOAc/Hex R$_f$ 0.28); $^1$H NMR (400 MHz, CDCl$_3$) δ 8.10 (br s, OH),), 7.11 (dd, J=8.3, 7.5 Hz, 1H), 6.76 (dd, J=8.3, 0.8 Hz, 1H), 6.64 (dd, J=7.5, 0.8 Hz, 1H), 5.63 (m, 1H), 5.02 (m, 2H), 3.61 (br s, 3H), 3.24 (d, J=10.8 Hz, 1H), 2.97 (br s, 3H), 2.94–2.85 (m, 2H), 2.35 (dd, J=10.8, 2.4 Hz, 1H), 2.24 (dd, J=10.8, 2.4 Hz, 1H), 1.96 (dd, J=12.5, 1.5 Hz, 1H), 1.74 (ddd, J=12.5, 5.6, 2.7 Hz, 1H).

Preparation of

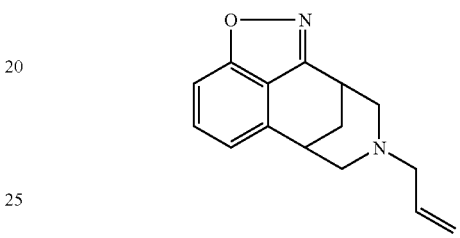

11-Allyl-6-hydroxy-11-aza-tricyclo[7.3.1.02,7]trideca-2, 4,6-trien-8-one oxime (100 mg, 0.39 mmol) and triethylamine (53 mg, 0.52 mmol) were dissolved in dichloromethane (5 mL) and treated with acetic anhydride (48 mg, 0.47 mmol). After stirring 3 h, the mixture was concentrated and dissolved in DMF (3 mL) then treated with NaH (60% in oil, ~100 mg, 2.5 mmol) under nitrogen (intermediate acetate TLC 5% EtOAc/dichloromethane R$_f$ 0.33). The foamy yellow mixture was stirred for 18 h, cooled and poured into 50% saturated aqueous NaCl solution (25 mL). The resulting mixture was extracted with 50% EtOAc/hexanes (4×25 mL) and the combined organic layer was washed with water (H$_2$O) (10 mL), saturated aqueous NaHCO$_3$ solution (10 mL) and saturated aqueous NaCl solution (10 mL), dried over Na$_2$SO$_4$, filtered, concentrated and purified by chromatography on silica gel eluting with 2% EtOAc/dichloromethane to provide an oil (71 mg, 76%). (TLC 5% EtOAc/dichloromethane R$_f$ 0.48); $^1$H NMR (400 MHz, CDCl$_3$) δ 7.43 (dd, J=8.3, 7.5 Hz, 1H), 7.28 (dd, J=8.3 Hz, 1H), 6.99 (d, J=7.5 Hz, 1H), 5.38 (m, 1H), 4.88 (d, J=10.2 Hz, 1H), 4.79 (d, J=17.2 Hz, 1H), 3.45 (t, J=10.2 Hz, 1H), 3.18 (t, J=10.2 Hz, 1H), 3.08 (d, J=11.0 Hz, 1H), 2.81 (m, 3H), 2.49 (m, 2H), 2.08 (AB m, 2H); GCMS m/z 240 (M)$^+$. A sample of this material was dissolved in a minimum of methanol then treated with 3N HCl EtOAc and concentrated to an oil which was dissolved in a minimum of EtOAc then treated with hexanes until cloudy and allowed to stir for 18 h. Product was collected by filtration. Mp=205–206° C.

EXAMPLE 9

Preparation of 9-Benzyl-9-aza-tricyclo[5.3.1.0$^{2,6}$] undec-3-ene (Based on Abdel-Magid, A. F.; Carson, K. G.; Harris, B. D.; Maryanoff, C. A.; Shah, R. D. *J. Org. Chem.* 1996, 61, 3849; and Mazzocchi, P. H.; Stahly, B. C. *J. Med. Chem.* 1979, 22, 455.)

3a,4,5,6,7,7a-Hexahydro-1H-4,7-methano-indene-5,6-diol (15.7 g, 96 mmol, prepared as described by Freeman, F.;

Kappos, J. C. *J. Org. Chem.* 1989, 54; 2730–2734) was stirred in H$_2$O (240 mL) and 1,2-dichloroethane (DCE) (80 mL) under nitrogen with a cool water bath (~10° C.). To this sodium periodate (NaIO$_4$) (21.4 g, 100 mmol) and triethylbenzyl ammonium chloride (Et$_3$BnNCl) (50 mg) were added. The resulting mixture was stirred for 1 h (slight initial exotherm), then the layers were separated and the aqueous layer extracted with DCE (3×50 mL). The organic layer was washed with H$_2$O (5×50 mL, or until no reaction to starch iodide is observed in the aqueous wash) then dried through a cotton plug. To this solution was added benzyl amine (11 mL, 100 mmol) and the mixture was stirred for 2 min. then immediately transferred into a slurried mixture of sodium triacetoxyborohydride NaBH(OAc)$_3$ (64.9 g, 0.306 mmol) in DCE (100 mL) stirred at 0° C. (ice bath) in a separate flask over 40 min. The resulting orange mixture was allowed to warm to room temperature and stirred for 75 min.

The reaction was carefully quenched by addition of saturated aqueous Na$_2$CO$_3$ solution (~100 mL) and the mixture was stirred for 1 h (pH 9). The layers were separated and the aqueous layer was extracted with dichloromethane (2×100 mL). The organic layer was washed with saturated aqueous NaCl solution (80 mL) and dried through a cotton plug. To this solution was added EtOAc (to make a ~10% solution) then the solution was filtered through a silica pad. Further elution with fresh 10% EtOAc/dichloromethane provided a solution of product free of baseline material. Evaporation gave an oily product (14.9 g, 66%). (TLC 10% EtOAc/dichloromethane R$_f$ 0.30); $^1$H NMR (400 MHz, CDCl$_3$) δ 7.39–7.30 (m, 5H), 5.96 (dd, J=5.6 Hz, 2.1 Hz, 1H), 5.67 (dd, J=5.6, 2.3 Hz, 1H), 3.42 (AB q, ΔAB=43.2 Hz, J=12.9 Hz, 2H), 3.28 (m, 1H), 2.78 (br d, J=12.4 Hz, 1H), 2.87 (m, 1H), 2.77 (br d, J=10.1 Hz, 1H), 2.46 (m, 1H), 2.37–2.14 (m, 5H), 1.82 (br d, J=10.8 Hz, 1H), 1.57 (d, J=10.8 Hz, 1H); APCl MS m/z 240.3 (M+1)$^+$; Anal. Calcd. for C$_{17}$H$_{21}$N: C, 85.30; H, 8.84; N, 5.85. Found C, 84.74; H, 8.52; N, 6.17. Calcd. for C$_{17}$H$_{21}$N.1/8H$_2$O C, 84.51; H, 8.87; N, 5.80. (Alternatively, dicyclopentadiene may be converted directly to the dialdehyde that is produced above, then converted as described to give the title compound. For methods see *Chem. Lett.* 1979, 443–446.)

Preparation of 9-Benzyl-9-aza-tricyclo[5.3.1.0$^{2,6}$]undecane-3,4-diol

9-Benzyl-9-aza-tricyclo[5.3.1.0$^{2,6}$]undec-3-ene (6.7 g, 28 mmol) and N-methyl morpholine N-oxide (3.45 g, 29.5 mmol) were stirred in acetone (50 mL) and H$_2$O (2 mL). To this was added osmium tetroxide (OSO$_4$, 1 mL of a 15 mol % t-butanol solution) and the mixture was stirred vigorously. After 7 h, the yellow solution was treated with a slurry of florisil in H$_2$O (5 g in 4 mL) and NaHSO$_3$ (2 g). After 1 h, the slurry was filtered through a Celite™ pad and concentrated. The residue was azeotropically dried by the addition of methanol and concentration in vacuo twice, the second time with silica gel, and the residue dry packed on silica gel (3×5 inch) and eluted with 50% EtOAc/hexane to generate pure product as an oil that crystallizes on standing (6.2 g, 80%). (TLC EtOAc R$_f$ 0.66); $^1$H NMR (400 MHz, CDCl$_3$) δ 7.30–7.20 (m, 3H), 7.16 (d, J=6.8 Hz, 2H), 4.38 (m, 2H), 3.34 (AB q, ΔAB=26.5, J=12.6 Hz, 2H), 2.83–2.73 (m, 2H), 2.65 (d, J=10.9 Hz, 1H), 2.43 (s, 1H), 2.37 (s, 1H), 2.22 (dd, J=11.3, 1.3 Hz, 1H), 2.13 (dd, J=10.9, 1.5 Hz, 1H), 2.01 (d, J=6.2 Hz, 1H), 1.75 (m, 2H), 1.75 (m, 1H), 1.57 (m, 1H); $^{13}$C NMR (100 MHz, CDCl$_3$) δ 139.4, 129.2, 128.1, 127.1, 80.3, 73.7, 63.1, 56.0, 55.4, 51.9, 43.3, 42.3, 35.2, 34.1, 30.6; GCMS m/z 273 (M)$^+$, 256 (M–OH)$^+$.

Preparation of 10-Benzyl-4,10-diaza-tricyclo[6.3.1.0$^{2,7}$]dodeca-2(7),3,5-triene 9-Benzyl-9-aza-tricyclo[5.3.1.0$^{2,6}$]undecane-3,4-diol (6.0 g, 22 mmol) was stirred in dioxane (50 mL) and treated with an aqueous solution of NaIO$_4$ (5.0 g, 23.4 mmol in 50 mL). A thick slurry forms and H$_2$O (50 mL) is added to aid stirring. After 30 min., dialdehyde has formed completely (TLC EtOAc R$_f$ 0.09) and the mixture is diluted with H$_2$O (150 mL) and saturated aqueous Na$_2$CO$_3$ solution (50 mL). Dialdehyde was extracted with EtOAc (2×150 mL) and the organic layer was washed with H$_2$O (150 mL) and saturated aqueous NaCl solution (50 mL). After drying over Na$_2$SO$_4$ the product was isolated by filtration and concentration to provide an orange oil (6.14 g).

The above oil was stirred in methanol (75 mL) and H$_2$O (75 mL) and treated with H$_2$NOCH$_3$.HCl (7.34 g, 87.9 mmol) and NaOAc (12.62 g, 154 mmol). The mixture was shaken and warmed on a steam bath until the cloudy mixture clears (~15 min.). This solution was stirred at ambient temperature 18 h. An oily residue had separated and after dilution with saturated aqueous Na$_2$CO$_3$ solution (100 mL) was extracted with EtOAc (3×50 mL). The organic layer was washed with saturated aqueous NaCl solution (50 mL), dried over Na$_2$SO$_4$, filtered and concentrated to give an oil (5.0 g, 69%), which was carried on in the next step. (TLC 15% EtOAc/hexane R$_f$ 0.50 and 0.35).

The above oil was dissolved in dichloroethane (150 mL) and trifluoroacetic acid (17 mL). After stirring 20 min. under nitrogen the mixture becomes light orange and was then warmed at reflux for 2 h. The resulting brown solution was stripped to an oil, dissolved in EtOAc (100 mL) and treated with saturated aqueous Na$_2$CO$_3$ solution (70 mL) causing the mixture to become light orange. The layers were separated and the organic layer washed with saturated aqueous NaCl solution (50 mL). After back extraction of the aqueous layer with EtOAc (3×30 mL) the organic layer was dried over Na$_2$SO$_4$, filtered and concentrated to an oil (4.0 g) which was purified on silica gel eluting with EtOAc to provide the title compound as an oil (1.94 g, 51%). (TLC 1% NH$_4$OH/7% MeOH/dichloromethane R$_f$ 0.75) (TLC EtOAc, R$_f$ 0.27); $^1$H NMR (400 MHz, CDCl$_3$) δ 8.44 (d, J=4.7 Hz, 1H), 8.35 (s, 1H), 7.25–7.07 (m, 4H), 6.85 (d, J=7.0 Hz, 2H), 3.45 (s, 2H), 3.14 (br s, 1H), 3.07 (br s, 1H), 2.79 (d, J=10.0 Hz, 2H), 2.41 (d, J=10.0 Hz, 2H), 2.21 (m, 1H), 1.69 (d, J=10.6 Hz, 1H); $^{13}$C NMR (CDCl$_3$, 100 MHz) δ 155.6, 148.0, 142.0, 138.5, 128,1, 127.9, 126.6, 117.3, 61.2, 55.9, 55.6, 43.6, 41.0, 38.9; GCMS m/z 250 (M)$^+$.

Preparation of 4,10-diaza-tricyclo[6.3.1.0$^{2,7}$]dodeca-2(7),3,5-triene dihydrochloride 10-Benzyl-4,10-diaza-tricyclo[6.3.1.0$^{2,7}$]dodeca-2(7),3, 5-triene (900 mg, 3.6 mmol) and HCO$_2$NH$_4$ (4 g) were dissolved in methanol (35 mL) and treated with Pd(OH)$_2$/C (10 wt %, 200 mg). The mixture was stirred and warmed to reflux for 2 h, cooled, filtered through Celite™ and rinsed with methanol. The filtrate was stripped, slurried in dichloromethane and filtered through a fritted-glass filter. The filtrate was concentrated and azeotroped from methanol (2×50 mL). A sample of this material was isolate and found to melt at 104–105° C. The material was dissolved in methanol and treated with 3N HCl/EtOAc. This was concentrated and azeotroped from methanol (2×50 mL). This residue was dissolved in a minimum of methanol then Et$_2$O until cloudy and allowed to stir for 60 h. Product was collected by filtration (370 mg, 52%). (TLC 1% NH$_4$OH/7% MeOH/dichloromethane R_f 0.18); ¹H NMR (400 MHz, CDCl₃) δ 8.88 (s, 1H), 8.83 (d, J=5.9 Hz, 1H), 8.16 (d, J=5.9 Hz, 1H), 3.75 (m, 2H), 3.60 (m, 2H), 3.40 (d, J=12.4 Hz, 2H), 2.57 (m, 1H), 2.34 (d, J=12.0 Hz, 1H); ¹³C NMR (100 MHz, CDCl₃, free base) δ 151.4, 149.5, 144.5, 137.7, 119.7, 45.8, 45.2, 41.0, 38.4, 36.4; GCMS m/z 160 (M)⁺; Anal. Calcd. for $C_{10}H_{12}N_2 \cdot 2$.HCl: C, 51.52; H, 6.05; N, 12.02. Found C, 51.35; H, 6.05; N, 12.05.

EXAMPLE 10

Preparation of 6-Methoxy-5,11-diaza-tricyclo[7.3.1.0²,⁷]trideca-2(7),3,5-triene-11-carboxylic acid tert-butyl ester To a round bottomed flask fitted with nitrogen inlet and stir bar was added 6-methoxy-5,11-diaza-tricyclo[7.3.1.0²,⁷]trideca-2(7),3,5-triene (100 mg, 0.49 mmol) from above, di-tert-butyl dicarbonate (120 mg, 0.54 mmol) NaHCO₃ (62 mg, 0.74 mmol) in 5 ml dichloromethane and water (1 ml). The reaction mixture was stirred vigorously under reflux for one hour. The reaction mixture was cooled to room temperature and then the layers were separated. The organic phase was partitioned between dichloromethane and brine and then dried over Na₂SO₄ and evaporated in vacuo to afford product (142 mg, 96%). ¹H NMR (CDCl₃, 400 MHz, ambient temperature) δ 7.84 (d, 1H, J=5 Hz), 6.61 (broadening due to slow rotation d, 1H, J=5 Hz), 4.27 (d, 1H, J=13 Hz), 4.07 (t, 1H), 3.84 (broadening due to slow rotation s, 3H), 3.05 (br.t, 1H), 2.90 (br.t, 1H), 2.80 (br.s, 1H), 2.70 (m, 1H), 2.20 (m, 1H), 1.85 (m, 2H), 1.10 (broadening due to slow rotation s, 9H); ¹³C NMR (CDCl₃, 100 MHz) δ 148.8, 147.0, 143.0, 142.4, 117.0, 116.7, 85.0, 53.1, 51.4, 50.3, 50.1, 49.1, 34.3, 29.3, 28.0, 27.8, 27.7, 27.5, 27.4, 27.3; APCl MS m/z 305 (M+1)⁺.

Preparation of 5-Methyl-6-oxo-5,11 I-diaza-tricyclo[7.3.1.0²,⁷]trideca-2(7), 3-diene-11-carboxylic acid tert-butylester To a thick wall Wheaton vial was added 6-methoxy-5,11-diaza-tricyclo[7.3.1.0²,⁷]trideca-2(7),3,5-triene-11-carboxylic acid tert-butyl ester (40 mg, 0.13 mmol and of methyl iodide (5 ml). The reaction mixture was heated in an oil bath at 130° C. for 4 h. The reaction mixture was cooled to room temperature and evaporated in vacuo. The residue was purified by chromatography on silica eluting with 98/2 dichloromethane/methanol to afford the desired product (22 mg, 56%). ¹H NMR (CDCl₃, 400 MHz, ambient temperature) δ 7.05 (d, 1H, J=7 Hz), 5.95 (broadening due to slow rotation, d, 1H, J=7 Hz), 4.09 (m, 1H), 3.45 (broadening due to slow rotation, s, 3H), 3.0 (m, 1H), 2.9 (m, 1H), 2.65 (m, 3H), 2.15 (m, 1H), 1.8 (m, 2H), 1.2 (broadening due to slow rotation, s, 9H); ¹³C NMR (CDCl₃, 100 MHz) δ 134.0, 107.0, 51.4, 50.0, 49.0, 47.9, 37.0, 34.6, 29.2, 27.9, 27.2; APCl MS m/z 305 (M+1)⁺.

Preparation of 5-Methyl-5,11-diaza-tricyclo[7.3.1.0²,⁷]trideca-2(7),3-dien-6-one To 5-methyl-6-oxo-5,11-diaza-tricyclo[7.3.1.0²,⁷]trideca-2(7),3-diene-11-carboxylic acid tert-butylester (22 mg, 0.07 mmol) (prepared above) was added anhydrous 3N HCl in ethyl acetate and the solution was stirred at room temperature for 16 h. The reaction mixture was evaporated in vacuo and the resulting white solid was recrystallized from methanol-ether to afford the desired product (9 mg, 64%). ¹H NMR (CD₃OD, 400 MHz) δ 7.53 (d, 1H, J=7 Hz), 6.25 (d, 1H, J=7 Hz), 3.54 (s, 3H), 3.3 (obsc. M, 4H), 3.08 (br.s, 1H), 2.85 (dd, 1H, J=19 Hz, J=7 Hz), 2.65 (d, 1H, J=19 Hz), 2.55 (br.s, 1H), 2.08 (d, 1H, J=13 Hz), 1.89 (d, 1H, J=13 Hz); APCl MS m/z 205 (M+1)⁺.

EXAMPLE 11

Preparation of 5,11-Diaza-tricyclo[7.3.1.0²,⁷]trideca-2(7),3-dien-6-one

To a flame dried round bottomed flask fitted with nitrogen inlet, stir bar and reflux condenser was added 6-methoxy-5,11-diaza-tricyclo[7.3.1.0²,⁷]trideca-2(7),3,5-triene-11-carboxylic acid tert-butyl ester (73 mg, 0.24 mmol) (prepared above) in dichloroethane (5 ml). The reaction mixture was treated with trimethylsilyliodide (206 uL, 1.44 mmol) and then heated under reflux for 2 h. After cooling to room temperature, the solution was evaporated in vacuo and replaced with methanol. This solution was heated under reflux for 2 h before cooling to room temperature and evaporation in vacuo. The residue was washed with ether and the ether phase was decanted. The oily residue was taken up in methanol and dried over Na₂SO₄ and then evaporated in vacuo to afford a yellow oil (35 mg, 78%). The oil was taken up in methanol and treated with HCl gas followed by precipitation with ether to afford HCl salt (6 mg). ¹H NMR (CD₃OD, 400 MHz) δ 7.56 (d, 1H, J=6 Hz), 6.66 (d, 1H, J=6 Hz), 3.3 (obsc. M, 5H), 2.94 (dd, 1H, J=19 Hz, J=7 Hz), 2.72 (d, 1H, J=19 Hz), 2.60 (br.s, 1H), 2.15 (d, 1H, J=13 Hz), 1.95 (d, 1H, J=13 Hz); APCl MS m/z 191 (M+1)⁺.

EXAMPLE 12

Preparation of Acetic acid bicyclo[2.2.1]hept-5-en-2-yl ester

To a solution of bicyclo[2.2.1]hept-5-en-2-ol (25 g) in 200 mL of anhydrous, dichloromethane is added triethylamine (30 mL) and 4-N,N-dimethylaminopyridine (30 mg). With stirring at room temperature and under an inert atmosphere, of acetic anhydride (35 mL) was added neat and dropwise to the above reaction mixture while maintaining the reaction at room temperature over 1.5 h. Upon complete addition of the anhydride the reaction is left for 3 h, the solvents were stripped and the crude mixture was purified by silica gel chromatography eluting with 25% ethyl acetate/hexanes to afford the title compound in a quantitative yield. ¹H NMR (CDCl₃, 400 MHz) δ 6.21 (m, 1H), 5.83 (m, 1H), 5.18 (m, 1H), 3.12 (d, 1H), 2.72 (d, 1H), 2.16 (s, 3H), 2.00 (m, 1H), 1.35 (m, 1H), 1.21 (m, 1H), 0.83 (m, 1H), APCl MS m/z 153.2 (M+H)⁺.

Preparation of Acetic acid 5,6-dihydroxy-bicyclo[2.2.1]hept-2-yl ester

To a solution of acetic acid bicyclo[2.2.1]hept-5-en-2-yl ester (10 mmol) and N-methyl morpholine N-oxide (22 mmol) in acetone (50 mL) and water (5 mL) was added osmium tetroxide (1.2 mL 2.5% by weight solution in t-butanol). The reaction mixture is allowed to stir at room temperature for 18 h and the acetone was stripped. Ethyl acetate (50 mL) and saturated sodium bicarbonate solution (50 ml) were added. The aqueous layer was extracted with ethyl acetate (4×50 mL). The combined organic extracts were washed with 1N aqueous HCl solution (2×50 mL) and the organic layer was dried over MgSO₄, filtered and concentrated to afford a yellow oil (8.3 mmol). ¹H NMR (CDCl₃, 400 MHz) δ 4.82 (m, 1H), 4.18 (m, 1H), 3.80–3.55 (br s, 3H), 2.40 (m, 2H), 2.00 (s, 3H), 1.80 (s, 1H), 1.19 (s, 2H), 0.80 (m, 1H); APCl MS m/z 187.3 (M+H)$^+$.

Preparation of Acetic acid
3-benzyl-3-aza-bicyclo[3.2.1]oct-6-yl ester

To a 0° C. solution of acetic acid 5,6-dihydroxy-bicyclo [2.2.1]hept-2-yl ester (8.3 mmol) in anhydrous dichloromethane (30 mL) and water (0.4 mL) was added solid NaIO$_4$ (10.8 mmol) portionwise so as not to allow the reaction to achieve room temperature. After complete addition and 4 h of vigorous stirring the reaction mixture is allowed to warm to room temperature and stir overnight. The reaction mixture was filtered through a pad of Celite™ and the salts were washed with an additional dichloromethane (80 mL). The filtrate was used in the next step without further purification.

To the above solution of acetic acid 2,4-diformyl-cyclopentyl ester was added at room temperature benzyl amine (5.8 mmol) and acetic acid (5.8 mmol) under nitrogen. After 2 h at room temperature sodium triacetoxy borohydride (25 mmol) was added and the reaction mixture was allowed to stir at room temperature for 18 h. The reaction mixture was quenched by the addition of saturated sodium bicarbonate solution (100 mL) and the phases were separated. The aqueous layer was extracted with dichloromethane (3×100 mL). The solvents were removed via rotary evaporation and the residue was purified by silica gel chromatography to afford a yellow oil (3.6 mmol). $^1$H NMR (CDCl$_3$, 400 MHz): δ 7.37 (m, 2H), 7.23 (m, 3H), 5.15–4.95 (m, 1H), 3.63–3.35 (m, 2H), 2.84–2.55 (m, 2H), 2.25–2.15 (m, 4H), 2.08 (s, 3H), 1.80–1.70 (m, 2H), 1.62–1.25 (m, 2H); APCl MS m/z 260.2 (M+H)$^+$.

Preparation of
3-Benzyl-3-aza-bicyclo[3.2.1]octan-6-ol

To a solution of acetic acid 3-benzyl-3-aza-bicyclo[3.2.1] oct-6-yl ester (8 mmol) in methanol (50 mL) and water (20 mL) was added potassium hydroxide (32 mmol). Reaction was stirred 18 h at room temperature. The methanol was removed in vacuo and product was extracted with aqueous dichloromethane (4×50 mL). The organic extracts were dried over MgSO$_4$, filtered and stripped to provide a quantitative yield of an oil. APCl MS m/z 218.2 (M+H)$^+$.

Preparation of
3-Benzyl-3-aza-bicyclo[3.2.1]octan-6-one

A solution of 3-benzyl-3-aza-bicyclo[3.2.1]octan-6-ol (8 mmol) in anhydrous dichloromethane at 0° C. under nitrogen was treated with of N-methyl morpholine N-oxide (12 mmol), 1 weight equivalent of oven dried 4 angstrom sieves and TPAP (tetrapropylammonium perruthenate) (0.2 mmol). The reaction mixture was stirred for 30 min. at 0° C. then allowed to warm to room temperature with stirring for an additional 1 h. The reaction was filtered through a plug of silica gel and eluted with ethyl acetate then striped to an oil. Purification by silica gel chromatography eluted with 15% ethyl acetate/hexanes produced an oil (7.7 mmol). APCl MS m/z 216.2 (M+H)$^+$.

Preparation of 3-Benzyl-7-dimethylaminomethylene-3-aza-bicyclo[3.2.1]octan-6-one To 3-benzyl-3-aza-bicyclo[3.2.1]octan-6-one (3.2 mmol) was taken up in Brederick's reagent (tris-(N,N-dimethylamino)methane, 10 mL) and heated for 8 h at 100° C. Excess Brederick's was removed in vacuo and the crude product was used as is in subsequent steps. $^1$H NMR (CDCl$_3$, 400 MHz) δ 7.50 (m, 5H), 3.56 (s, 3H), 2.99 (s, 6H), 2.40–2.20 (m, 4H), 1.95 (m, 2H), 2.56 (m, 2H); APCl MS m/z 271.3 (M+H)$^+$.

Preparation of 5,14-Diazatetracyclo[10.3.1.0$^{2,11}$.0$^{4,}$
$_9$]-14 benzyl hexadeca-2(11),3,5,7,9-pentane To a solution of 3-benzyl-3-aza-bicyclo[3.2.1]octan-6-one (2.58 mmol) in acetic acid (3 ml) and sulphuric acid (0.14 ml) was added 2-amino benzaldehyde (2.58 mmol). The reaction mixture was warmed to 100° C. for 60 h. The solvent was removed in vacuo and the residue was partitioned between 2 N aqueous NaOH and dichloromethane The dichloromethane layer was dried over MgSO$_4$, filtered and stripped to furnish an oil. Purification by flash chromatography eluting with 10% MeOH/ethyl acetate yielded product (0.9 mmol). $^1$H NMR (CDCl$_3$, 400 MHz) δ 8.06 (m, 1H), 7.74 (m, 2H), 7.62 (m, 1H), 7.48 (m, 1H), 7.10 (m, 3H), 6.80 (m, 2H), 3.50–3.38 (m, 4H), 3.20 (m, 1H), 2.90 (m, 1H), 2.60–2.50 (m, 2H), 2.30 (m, 1H), 1.84 (m, 1H); APCl MS m/z 301.2 (M+H)$^+$.

Preparation of 5,14-Diazatetracyclo [10.3.1.0$^{2,11}$.0$^{4,}$
$_9$]-hexadeca-2(11),3,5,7,9-pentane hydrochloride A solution of 5,14-diazatetracyclo [10.3.1.0$^{2,11}$.0$^{4,9}$]-14 benzyl hexadeca-2(11),3,5,7,9-pentane (0.50 mmol) in chloroethyl chloroformate (4 ml) was brought to 100° C. for 18 h. Excess solvent was removed in vacuo and the residue was dissolved in methanol (5 mL) and brought to reflux for 4 h. The reaction mixture was cooled and the solvents removed in vacuo to yield an oily solid. The solids were triturated with diethyl ether and collected to yield product (0.45 mmol). $^1$H NMR (CD$_3$OD, 400 MHz) δ 8.80 (s, 1H), 8.20 (m, 2H), 8.10 (m, 2H), 7.85 (m, 1H), 3.80 (br d, 2H), 2.75–2.50 (m, 2H), 3.45 (m, 2H), 2.62 (m, 1H), 2.40 (m, 1H); APCl MS m/z 211.2 (M+H)$^+$.

EXAMPLE 13

Preparation of 10-Benzyl-4-methyl-3,5,10-triaza-tricyclo[6.3.1.0$^{2,7}$]dodeca-2(7), 3,5-triene To a solution of 3-benzyl-7-dimethylaminomethylene-3-aza-bicyclo[3.2.1]octan-6-one (1.42 mmol) in ethanol was added potassium carbonate (3.8 mmol) and acetamidine hydrochloride (1.6 mmol). The reaction mixture was heated under reflux overnight. After cooling the solvents were removed and dichloromethane and aqueous sodium bicarbonate solution were added. The dichloromethane layer was separated and dried to an oil. Purification by flash chromatography on silica gel eluted with ethyl acetate yielded product (0.23 mmol). $^1$H NMR (CD$_3$OD, 400 MHz) δ 8.25 (s, 1H), 7.18 (br s, 3H), 6.85 (br s, 2H), 3.60–3.40 (m, 2H), 3.10 (s, 1H), 3.00 (m, 2H), 2.79 (m, 1H), 2.70 (s, 3H), 2.5 (m, 1H), 2.45 (m, 1H), 2.25 (m, 1H), 1.70 (m, 1H); APCl MS m/z 266.2 (M+H)$^+$.

Preparation of 4-Methyl-3,5,10-triaza-tricyclo
[6.3.1.0$^{2,7}$]dodeca-2(7),3,5-triene-10-carboxylic acid
tert-butyl ester To a solution of 10-benzyl-4-methyl-3,5,10-triaza-tricyclo [6.3.1.0$^{27}$]dodeca-2(7),3,5-triene (0.23 mmol) in ethanol (5 ml) was added ammonium formate (1.15 mmol), di-t-butyl carbonate (2.3 mmol) and of Pearlman's catalyst (3 mg). The mixture was heated at reflux for 18 h, cooled and filtered through a Celite™ pad which was washed with methanol. The filtrate was stripped of solvent and the residue was purified by flash chromatography on silica gel eluting with ethyl acetate to yield product (0.1 mmol). $^1$H NMR (CD$_3$OD, 400 MHz) δ 8.35 (s, 1H), 4.15–3.95 (m, 2H), 3.30–3.00 (m, 4H), 2.70 (s, 3H), 2.35 (m, 1H), 1.85 (m, 1H), 1.25 (br s, 9H); APCl MS m/z 276.2 (M+H)$^+$.

Preparation of 4-Methyl-3,5,10-triaza-tricyclo [6.3.1.0$^{2,7}$]dodeca-2(7),3,5-triene To a solution of 4-methyl-3,5,10-triaza-tricyclo[6.3.1.0$^{2,7}$] dodeca-2(7),3,5-triene-10-carboxylic acid tert-butyl ester (0.1 mmol) in methanol (2 ml) was added a solution of 1N HCl in methanol (2 mL). The reaction mixture was stirred for 3 h at room temperature and the solvents were removed to leave a solid (0.1 mmol). $^1$H NMR (CD$_3$OD, 400 MHz) δ 8.40 (s, 1H), 4.20–3.80 (m, 2H), 3.40–3.00 (m, 4H), 2.60 (s, 3H), 2.10 (m, 1H), 0.80 (br s, 1H); APCl MS m/z 176.2 (M+H)$^+$.

EXAMPLE 14

Preparation of 9-Benzyl-3-(4-fluoro-phenyl)-3,4,9-triaza-tricyclo[5.3.1.0$^{2,6}$]undeca-2(6),4-diene To a solution of 3-benzyl-7-dimethylaminomethylene-3-aza-bicyclo[3.2.1]octan-6-one (0.6 mmol) in ethanol (3 mL) was added (4-fluoro-phenyl)-hydrazine hydrochloride (0.7 mmol). The reaction mixture was heated at reflux overnight, cooled, concentrated and the residue was treated with dichloromethane and aqueous sodium bicarbonate solution. The aqueous layer was extracted with dichloromethane and the organic layer was dried and stripped to provide an oil that was purified by flash chromatography on silica gel eluting with 20% ethyl acetate/hexanes to yield product (0.23 mmol). $^1$H NMR (CDCl$_3$, 400 MHz) δ 7.55 (m, 2H), 7.40 (s, 1H), 7.20–6.90 (m, 7H), 3.50 (br s, 2H), 3.25 (br s, 1H), 3.10 (br s, 1H), 2.95–2.6.

Preparation of 3-(4-Fluoro-phenyl)-3,4,9-triaza-tricyclo[5.3.1.0$^{2,6}$]undeca-2(6),4-diene To a solution of 9-benzyl-3-(4-fluoro-phenyl)-3,4,9-triaza-tricyclo[5.3.1.0$^{20}$.6]undeca-2(6),4-diene (0.23 mmol) in methanol (2 ml) was added a solution of 1N HCl in diethyl ether (2 mL). The mixture was stirred for 45 min. and the solvent was removed to yield a solid. In a separate flask piperdine (1.5 mmol) and formic acid (0.69 mmol) were combined in methanol (2 ml). To this solution is added a solution of the HCl salt of 9-benzyl-3-(4-fluoro-phenyl)-3,4, 9-triaza-tricyclo[5.3.1.0$^{2,6}$]undeca-2(6),4-diene in methanol (3 ml). To this resulting solution was added Pearlman's catalyst (8 mg, 10% wt. on carbon). The reaction mixture was heated under reflux under a nitrogen atmosphere for 18 h then it was cooled and filtered through a plug of Celite™ to remove solids and the pad was washed with methanol. The resulting filtrate was condensed to a gum, which is taken up in ethyl acetate and saturated aqueous sodium bicarbonate solution (20 ml). The mixture was extracted with ethyl acetate (3×20 mL) and the resulting organic layer was dried over MgSO$_4$. The solids were removed by vacuum filtration and the solvent was removed to provide an oil which was purified by chromatography on silica gel eluting with 0.1% ammonium hydroxide solution in 10% methanol/dichloromethane to produce an oil that was treated with 1N HCl in ethyl ether. Trituration of the solids produced a gummy solid (0.082 mmol). $^1$H NMR (CD$_3$OD, 400 MHz) δ 7.60 (m, 2H), 7.40 (s, 1H), 7.20 (br, 2H), 3.25 (m, 1H), 2.90–2.60 (m, 5H), 2.20 (m, 1H), 0.80 (br s, 1H); APCl MS m/z 244.2 (M+H)$^+$.

EXAMPLE 15

Preparation of 5,7-Dibromo-3,14-Diazatetracyclo [10.3.1.0$^{2,11}$.0$^{4,9}$]-14 benzyl hexadeca-2(11),3,5,7,9-pentane Following the method described in Example 13, 5,14-diazatetracyclo [10.3.1.0$^{2,11}$.0$^{4,9}$]-14 benzyl hexadeca-2(11),3, 5,7,9-pentane and 3,5-dibromo-2-amino benzaldehyde were converted to the title compound in 30% overall yield. APCl MS m/z 369.0 (M+H)$^+$.

EXAMPLE 16

Preparation of 3,5,10-Triaza-tricyclo[6.3.1.0$^{2,7}$] dodeca-2(7),3,5-trien-4-ylamine Following the method described in Example 13, 10-benzyl-4-methyl-3,5,10-triaza-tricyclo[6.3.1.0$^{2,7}$]dodeca-2(7), 3,5-triene and formamidine acetate were converted to the title compound in 18% overall yield. APCl MS m/z 177.1 (M+H)$^+$.

EXAMPLE 17

Preparation of 4-Phenyl-3,5,10-triaza-tricyclo [6.3.1.0$^{2,7}$]dodeca-2(7),3,5-triene Following the method described in Example 13, 10-benzyl-4-methyl-3,5,10-triaza-tricyclo[6.3.1.0$^{2,7}$]dodeca-2(7), 3,5-triene and phenyl amidine were converted to the title compound in 9% overall yield. APCl MS m/z 238.1 (M+H)$^+$.

EXAMPLE 18

Preparation of 4-Pyridin-4-yl-3,5,10-triaza-tricyclo [6.3.1.0$^{2,7}$]dodeca-2(7),3,5-triene Following the method described in Example 13, 10-benzyl-4-methyl-3,5,10-triaza-tricyclo[6.3.1.0$^{2,7}$]dodeca-2(7), 3,5-triene and isonicotinamidine were converted to the title compound in 7.5% overall yield. APCl MS m/z 239.1 (M+H)$^+$.

EXAMPLE 19

Preparation of 3-tert-Butyl-3,4,9-triaza-tricyclo[5.3.1.0 $^{2,6}$]undeca-2(6),4-diene Following the method described in Example 14, 3-benzyl-7-dimethylaminomethylene-3-aza-bicyclo[3.2.1]octan-6-one and t-butyl hydrazine were converted to the title compound in 7.5% overall yield. APCl MS m/z 206.2 (M+H)$^+$.

EXAMPLE 20

Preparation of 3-Pyridin-2-yl-3,4,9-triaza-tricyclo [5.3.1.0$^{2,6}$]undeca-2(6),4-diene Following the method described in Example 14, 3-benzyl-7-dimethylaminomethylene-3-aza-bicyclo[3.2.1]octan-6- one and 2-pyridyl hydrazine were converted to the title compound in 7.6% overall yield. APCl MS m/z 227.2 $(M+H)^+$.

What is claimed is:

1. The (−)-isomers and the (+)-isomers of the following compounds;

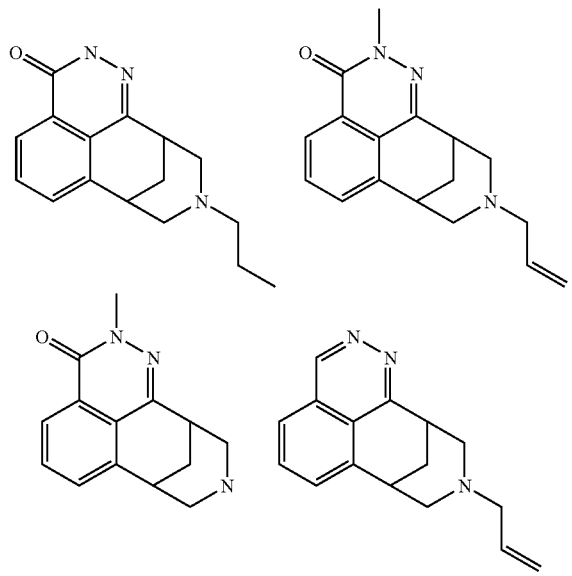

-continued

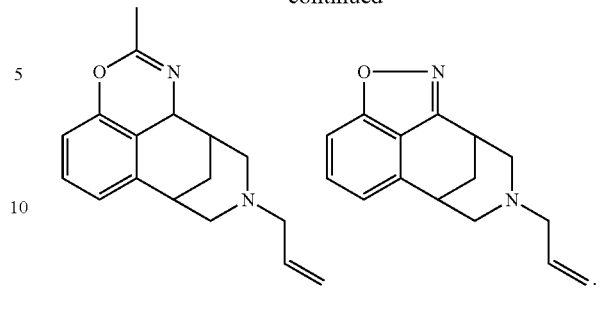

2. A pharmaceutical composition for suppressing nicotine binding to specific nicotine receptor sites in vitro, comprising an amount of a compound according to claim 1 that is effective in suppressing nicotine binding to specific nicotine receptor sites and a pharmaceutically acceptable carrier.

3. A method for suppressing nicotine binding to specific nicotine receptor sites in vitro, comprising an amount of a compound according to claim 1 that is effective in suppressing nicotine binding to specific nicotine receptor sites.

* * * * *